US008530236B2

(12) United States Patent
Fadeev et al.

(10) Patent No.: US 8,530,236 B2
(45) Date of Patent: Sep. 10, 2013

(54) SWELLABLE (METH)ACRYLATE SURFACES FOR CULTURING CELLS IN CHEMICALLY DEFINED MEDIA

(71) Applicants: Andrei Gennadyevich Fadeev, Elmira, NY (US); Arthur Winston Martin, Horseheads, NY (US); Zara Melkoumian, Corning, NY (US); Christopher Bankole Shogbon, Corning, NY (US); David Michael Weber, Big Flats, NY (US); Jennifer Lynn Weber, Big Flats, NY (US); Yue Zhou, Horseheads, NY (US)

(72) Inventors: Andrei Gennadyevich Fadeev, Elmira, NY (US); Arthur Winston Martin, Horseheads, NY (US); Zara Melkoumian, Corning, NY (US); Christopher Bankole Shogbon, Corning, NY (US); David Michael Weber, Big Flats, NY (US); Jennifer Lynn Weber, Big Flats, NY (US); Yue Zhou, Horseheads, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 13/668,867

(22) Filed: Nov. 5, 2012

(65) Prior Publication Data
US 2013/0203165 A1 Aug. 8, 2013

Related U.S. Application Data

(62) Division of application No. 12/362,974, filed on Jan. 30, 2009, now Pat. No. 8,329,469.

(60) Provisional application No. 61/062,890, filed on Jan. 30, 2008, provisional application No. 61/062,937, filed on Jan. 30, 2008.

(51) Int. Cl.
*C12N 5/00* (2006.01)
*C12N 11/00* (2006.01)

(52) U.S. Cl.
USPC .......................................... 435/395; 435/174

(58) Field of Classification Search
USPC ................................................ 435/395, 174
See application file for complete search history.

(56) References Cited

U.S. PATENT DOCUMENTS

| 4,578,079 | A | 3/1986 | Ruoslahti et al. ............. 523/11 |
|---|---|---|---|
| 4,792,525 | A | 12/1988 | Ruoslahti et al. ....... 435/240.243 |
| 4,908,236 | A | 3/1990 | Pitt et al. ...................... 427/245 |
| 5,278,063 | A | 1/1994 | Hubbell et al. ......... 435/240.243 |
| 5,330,911 | A | 7/1994 | Hubbell et al. ......... 435/240.243 |
| 5,480,953 | A | 1/1996 | Sugaya et al. ................. 526/320 |
| 5,643,561 | A | 7/1997 | Katsuen et al. ............. 424/78.17 |
| 5,691,203 | A | 11/1997 | Katsuen et al. ................ 435/402 |
| 5,695,997 | A | 12/1997 | Ruoslahti et al. .............. 435/375 |
| 5,916,875 | A | 6/1999 | Ruoslahti et al. ................ 514/12 |
| 6,121,027 | A | 9/2000 | Clapper et al. ................. 435/180 |
| 6,306,922 | B1 | 10/2001 | Hubbell et al. .................. 522/71 |
| 8,298,606 | B2 * | 10/2012 | Healy et al. ..................... 427/2.1 |
| 2010/0099160 | A1 * | 4/2010 | Jiang et al. ..................... 435/180 |

FOREIGN PATENT DOCUMENTS

| EP | 0614923 B1 | 1/2000 |
|---|---|---|
| JP | 01-309682 | 12/1989 |
| JP | 2002-191353 | 7/2002 |
| JP | 2006-042794 | 2/2006 |
| JP | 2006-174826 | 7/2006 |
| WO | 98/31734 | 7/1998 |

OTHER PUBLICATIONS

Anderson, Daniel G., Levenberg, Shulamit, Langer, Robert, Nanoliter-scale synthesis of arrayed biomaterials and application to human embryonic stem cells, Nature Biotechnology vol. 22, No. 7, Jul. 2004, 863-866.

Barber, T.A., Harbers, G.M., Park, S., Gilbert, M., Healy, K.E., "Ligand Density Characterization of Peptide-Modified Biomaterials," Biomaterials, 26(34), 6897-6905 (2005).

Barber, T.A., Golledge, S.L., Castner, D.G, and Healy, K.E., "Peptide-modified p(AAm-co-Eg/AAc) IPNS Grafted to Bulk Titanium Modulate Osteoblast Behavior in Vitro," J. Biomed. Mater. Res., 64A, 38-47 (2003).

Bearinger, J.P., Castner, D.G., and Healy, K.E., "Biomolecular Modification of P(AAm-co-Eg/AA) IPNs Supports Osteoblast Adhesion and Phenotypic Expression," J. Biomaterials Science:Polymer Ed., 9(7), 629-652 (1998).

Bearinger, J.P., Castner, D.G., Chen, J., Hubchak, S., Golledge, S.L., and Healy, K.E., "P(AAm-co-EG) Interpenetrating Polymer Networks Grafted to Oxide Surfaces: Surface Characterization, Protein Adsorption, and Cell Detachment Studies," Langmuir, 13(19), 5175-5183 (1997).

Braam, Stefan R., et al., Recombinant Vitronectin Is a Functionally Defined Substrate that Supports Human Embryonic Stem Cell Self Renewal Via AVB5 Integrin, Stem Cells express, Jul. 3, 2008, 1-20.

(Continued)

*Primary Examiner* — Karen Cochrane Carlson
*Assistant Examiner* — Natalie Moss
(74) *Attorney, Agent, or Firm* — Susan S. Wilks

(57) ABSTRACT

Synthetic surfaces capable of supporting culture of undifferentiated human embryonic stem cells in a chemically defined medium include a swellable (meth)acrylate layer and a peptide conjugated to the swellable (meth)acrylate layer. The swellable (meth)acrylate layer may be formed by polymerizing monomers in a composition that includes hydroxyethyl methacrylate, 2-carboxyehylacrylate, and tetra(ethylene glycol)dimethacrylate. The conjugated peptide may include an amino acid sequence of $Xaa_n$ProGlnValThrArgGlyAspValPheThrMetPro, where n is an integer from 0 to 3 and where Xaa is any amino acid. Further, disclosed herein is a swellable (meth)acrylate synthetic surface which can be sterilized by gamma irradiation.

17 Claims, 13 Drawing Sheets

(56) References Cited

OTHER PUBLICATIONS

Brandley, B.K., et al., "Covalent Attachment of an Arg-Gyl-Asp Sequence Peptide to Derivatizable Polyacrylamide Surfaces: Sequence Peptide to Derivatizable Polyacrylamide Surfaces: Support of Fibroblast Adhesion and Long-Term Growth", Analytical Biochemistry, vol. 172, 1988, 270-278.

Tanahashi et al, "Protien adsorption and smooth muscle cell adhesion on biodegradable agmatine-modified poly(propylene fumarate-co-ethylene glycol) hydrogels", J. of Biomedical Materials Research, vol. 67, No. 2, Nov. 1, 2003 pp. 448-457.

Shin et al, "Attachment, proliferation and migration of marrow stromal osteoblasts cultured on biomimetic hydrogels modified with an osteopontin-derived peptide", Biomaterials, Elsevier Science, vol. 25, No. 5, Feb. 1, 2004, pp. 865-906.

Kroupova, et al, "Functional polymer hydrogels for embryonic stem cell support", J. of Biomedical Materials Research, vol. 76B, No. 2, Feb. 1, 2006, pp. 315-325.

Horak et al, "Poly(2-hydroxyethyl methacrylate)-based slabs as a mouse embryonic stem cell support", Biomaterials, vol. 25, No. 22, Oct. 1, 2004, pp. 5249-5260.

Fassler et al, "Lack of beta-1 integral gene in embryonic stem cells affects morphology, adhesion, and migration but not integration into the inner cell mass of blastocysts" J. of Cell Biology, vol. 128 No. 5, Jan. 1, 1005, pp. 979-988.

\* cited by examiner

SEQUENCE LISTING

<160> NUMBER OF SEQ ID NOS: 7

<210> SEQ ID NO 1
<211> LENGTH: 15
<212> TYPE: PRT
<213> ORGANISM: artificial
<220> FEATURE:
<223> OTHER INFORMATION: Synthetic polypeptide (vitronectin)
<220> FEATURE:
<221> NAME/KEY: MISC_FEATURE

```
<222> LOCATION: (1)..(3)
<223> OTHER INFORMATION: Xaa at positions 1-3 may be any amino acid
<220> FEATURE:
<221> NAME/KEY: MISC_FEATURE
<222> LOCATION: (1)..(3)
<223> OTHER INFORMATION: Xaa at positions 1-3 may be absent

<400> SEQUENCE: 1

Xaa Xaa Xaa Pro Gln Val Thr Arg Gly Asp Val Phe Thr Met Pro
1               5                   10                  15

<210> SEQ ID NO 2
<211> LENGTH: 15
<212> TYPE: PRT
<213> ORGANISM: artificial
<220> FEATURE:
<223> OTHER INFORMATION: Synthetic polypeptide (bsp)
<220> FEATURE:
<221> NAME/KEY: MISC_FEATURE
<222> LOCATION: (1)..(1)
<223> OTHER INFORMATION: Xaa at position 1 may be any amino acid

<400> SEQUENCE: 2

Xaa Gly Gly Asn Gly Glu Pro Arg Gly Asp Thr Tyr Arg Ala Tyr
1               5                   10                  15

<210> SEQ ID NO 3
<211> LENGTH: 9
<212> TYPE: PRT
<213> ORGANISM: artificial
<220> FEATURE:
<223> OTHER INFORMATION: Synthetic polypeptide (scrambled RGD)

<400> SEQUENCE: 3

Arg Gly Gly Ser Asp Pro Ile Tyr Lys
1               5

<210> SEQ ID NO 4
<211> LENGTH: 9
<212> TYPE: PRT
<213> ORGANISM: artificial
<220> FEATURE:
<223> OTHER INFORMATION: Synthetic polypeptide (labeled RGD)

<400> SEQUENCE: 4

Gly Arg Gly Asp Ser Pro Ile Ile Lys
1               5

<210> SEQ ID NO 5
<211> LENGTH: 15
<212> TYPE: PRT
<213> ORGANISM: artificial
<220> FEATURE:
<223> OTHER INFORMATION: Synthetic polypeptide (vitronectin)

<400> SEQUENCE: 5

Lys Gly Gly Pro Gln Val Thr Arg Gly Asp Val Phe Thr Met Pro
1               5                   10                  15

<210> SEQ ID NO 6
<211> LENGTH: 15
<212> TYPE: PRT
<213> ORGANISM: artificial
<220> FEATURE:
<223> OTHER INFORMATION: Synthetic polypeptide (bsp)

<400> SEQUENCE: 6

Lys Gly Gly Asn Gly Glu Pro Arg Gly Asp Thr Tyr Arg Ala Tyr
1               5                   10                  15
```

```
<210> SEQ ID NO 7
<211> LENGTH: 15
<212> TYPE: PRT
<213> ORGANISM: artificial
<220> FEATURE:
<223> OTHER INFORMATION: Synthetic polypeptide (vitronectin)
<220> FEATURE:
<221> NAME/KEY: misc_feature
<222> LOCATION: (1)..(1)
<223> OTHER INFORMATION: Xaa can be any naturally occurring amino acid

<400> SEQUENCE: 7

Xaa Gly Gly Pro Gln Val Thr Arg Gly Asp Val Phe Thr Met Pro
1               5                   10                  15
```

SWELLABLE (METH)ACRYLATE SURFACES FOR CULTURING CELLS IN CHEMICALLY DEFINED MEDIA

This application is a Divisional of U.S. patent application Ser. No. 12/362,974 filed on Jan. 30, 2009, which claims the benefit of U.S. Provisional Application Ser. No. 61/062,890 filed Jan. 30, 2008 and entitled "Synthetic Surfaces for Culturing Undifferentiated Stem Cells in Chemically Defined Media" and U.S. Provisional Application Ser. No. 61/062, 937 filed Jan. 30, 2008 and entitled "Stem Cell Article and Screening", the content of which is relied upon and incorporated herein by reference in its entirety, and the benefit of priority under 35 U.S.C. §120 is hereby claimed.

SEQUENCE LISTING

The instant application contains a Sequence Listing which has been submitted in ASCII format via EFS-Web and is hereby incorporated by reference in its entirety. Said ASCII copy, created on Jan. 30, 2009, is named SP09014US.txt and is 3 KB in size.

FIELD

The present disclosure relates to cell culture articles, and more particularly to synthetic surfaces and articles for supporting the culture of undifferentiated stem cells in a chemically defined medium.

BACKGROUND

Pluripotent stem cells such as human embryonic stem cells (hESCs) have the ability to differentiate into any of the three germ layers, giving rise to any adult cell type in human body. This unique property provides a potential for developing new treatments for a number of serious cell degenerative diseases, such as diabetes, spinal chord injury, heart diseases and the like. However there remain obstacles in the development of such hESC-based treatments. Such obstacles include obtaining and maintaining adequate numbers of undifferentiated hESCs in cell and tissue culture and controlling their differentiation in order to produce specific cell types. Stem cell cultures, such as hESC cell cultures are typically seeded with a small number of cells from a cell bank or stock and then amplified in the undifferentiated state until differentiation is desired for a given therapeutic application. To accomplish this, the hESC or their differentiated cells are currently cultured in the presence of surfaces or media containing animal-derived components, such as feeder layers, fetal bovine serum, or MATRIGEL®. These animal-derived additions to the culture environment expose the cells to potentially harmful viruses or other infectious agents which could be transferred to patients or compromise general culture and maintenance of the hESCs. In addition, such biological products are vulnerable to batch variation, immune response and limited shelf-life.

To date, a completely animal product free system employing a chemically defined medium and a synthetic surface has not yet been identified for supporting long-term culture of undifferentiated stem cells.

BRIEF SUMMARY

In embodiments, synthetic surfaces of the present invention may be useful to provide for the culture of undifferentiated human embryonic stem cells or other cells for more than five passages, in the presence of chemically defined media. In additional embodiments, synthetic surfaces of the present invention may be sterilizable using irradiation techniques including gamma irradiation and E-beam irradiation.

In embodiments of the present invention, a method for culturing an isolated population of undifferentiated human embryonic stem cells in chemically defined medium on a synthetic culture surface that has been sterilized by gamma irradiation is provided. In additional embodiments, the culture of isolated undifferentiated human embryonic stem cells may remain viable for at least five passages.

A cell culture article includes a substrate having a surface. In embodiments of the present invention, a swellable (meth) acrylate layer is disposed on the surface of the cell culture substrate. The swellable (meth)acrylate layer may be formed from a composition that includes hydroxyethyl methacrylate, 2-carboxyethylacrylate, and tetra(ethylene glycol) dimethacrylate. In additional embodiments, a polypeptide may be conjugated to the swellable acrylate layer. The polypeptide may include an amino acid sequence of Xaa$_n$Pro-GlnValThrArgGlyAspValPheThrMetPro (SEQ ID NO:1), where n is an integer from 0 to 3, and Xaa$_n$ is any amino acid. In embodiments, Xaa$_n$ may be LysGlyGly, (LysGlyGlyPro-GlnValThrArgGlyAspValPheThrMetPro (SEQ ID NO:5). n embodiments, the cell culture article may be sterilizable using gamma radiation sterilization techniques. In additional embodiments, the cell culture article may support culture and maintenance of undifferentiated stem cells, such as human embryonic stem cells, in a chemically defined medium.

In various embodiments, a method for producing a cell culture article includes disposing monomers on a substrate surface of the cell culture article. The monomers disposed on the surface include 2-carboxyethylacrylate, tetra(ethylene glycol)dimethacrylate, and one of hydroxyethyl methacrylate, hydroxypropyl methacrylate, 2-hydroxyethyl acrylate, 1-vinyl-2-pyrrolidone, di(ethylene glycol) ethyl ether methacrylate, acrylamide, ethylene glycol methyl ether methacrylate or 3-sulfopropyldimethyl-3-methacrylamidopropyl-ammonium. The method further includes polymerizing the monomers on the substrate surface to form a swellable (meth) acrylate layer. The method also includes conjugating to the acrylate layer a polypeptide including an amino acid sequence of Xaa$_n$ProGlnValThrArgGlyAspVal-PheThrMetPro (SEQ ID NO:1), Xaa is any amino acid and n is an integer from 0 to 3, which may be a polypeptide having an amino acid sequence of XaaGlyGlyProGlnValThrArgGl-yAspValPheThrMetPro (SEQ ID NO:7), where Xaa may be any amino acid. In embodiments, Xaa is Lys LysGlyGlyPro-GlnValThrArgGlyAspValPheThrMetPro (SEQ ID NO:5).

One or more of the various embodiments presented herein provide one or more advantages over prior surfaces for culturing stem cells, particularly undifferentiated stem cells. For example, synthetic surfaces reduce potential contamination issues associated with surfaces having components obtained from or derived from animal sources. Such surfaces may also provide for improved shelf life compared to those surfaces with biological components. Embodiments of synthetic surfaces of the present invention may survive sterilization treatments by irradiation including e-beam or gamma irradiation.

In additional embodiments, the ability to culture undifferentiated stem cells in chemically-defined media further reduces potential contamination issues. In addition, there will likely be less batch-to-batch variation in the synthetic surfaces and chemically defined media, resulting in improved reproducibility of culture results and expectations. These and other advantages will be readily understood from the following detailed descriptions when read in conjunction with the accompanying drawings

BRIEF DESCRIPTION OF THE DRAWINGS

FIGS. 7A and B show cells growing on SAP-BSP surfaces, and FIGS. 7C and C show cells growing on SAP-VN surfaces.

Figure 3A:
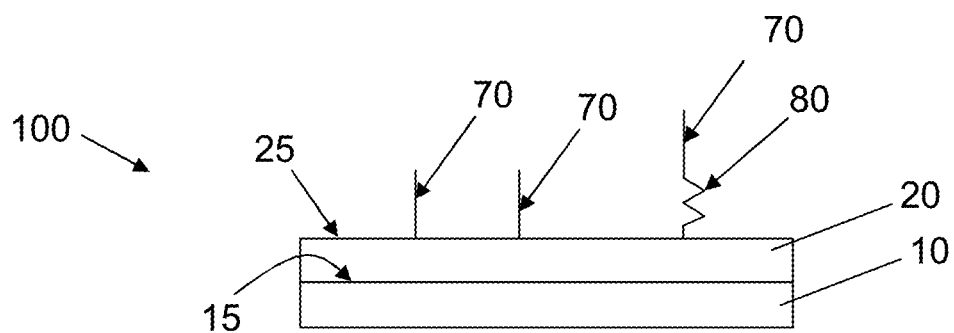
FIGS. 3A-B are schematic diagrams of side views of embodiments of synthetic swellable acrylate coated articles.
Figure 3B:
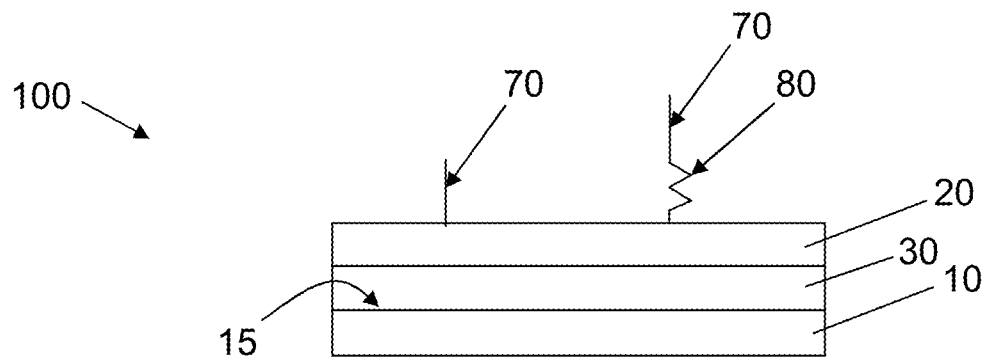
Figure 4A:
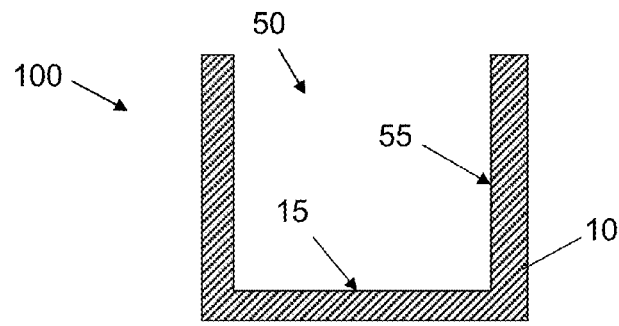
FIG. 4A-C are schematic diagrams of cross sections of cell culture articles having a well. Uncoated (4A); coated surface (4B); and coated surface and side walls (4C).

The drawings depicted in FIGS. 3-4 are not necessarily to scale. Like numbers used in the FIGS. 3-4 refer to like components. However, it will be understood that the use of a number to refer to a component in a given figure is not intended to limit the component in the other figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to".

The term "hydrogel" has been used to describe cell culture surfaces. "Hydrogel" has been variously defined to include a gel or gelatin that can absorb water in an amount greater than or equal to 30% or up to 10,000% of its dry weight. Hydrogels have been classified according to water content. For example, hydrogels have been described as absorbing 30% water or more. When contacted with water, hydrogels swell but do not dissolve. The term "hydrogel" is a very broad term, describing a wide range of materials, having a wide range of water swelling and water absorbing characteristics.

As used herein, "swellable (meth)acrylate" or "SA" means a polymer matrix made from at least one ethylenically unsaturated monomer (acrylate or methacrylate monomers) having at least some degree of cross linking, and also having water absorbing or water swelling characteristics. In embodiments, the swellable (meth)acrylates of the present invention are synthetic. That is, they do not contain ingredients that are derived from animals or animal extracts. Embodiments of swellable (meth)acrylates may be conjugated to peptides or proteins ("swellable (meth)acrylate-peptide" or "SAP"). Peptides or proteins may be synthesized or obtained through recombinant techniques, making them synthetic, non-animal-derived materials. This SA and SAP material may be referred to as a layer, a coating, a surface, a material, or any other term known in the art to refer to a surface suitable for cell culture. The particular peptide sequence may be further identified. For example, a SAP surface may be conjugated with a vitronectin peptide sequence and may be identified as SAP-VN. In embodiments of the present invention, the term "swellable (meth)acrylate" represents a range of cross-linked acrylate or methacrylate materials which absorb water, swell in water, and do not dissolve in water. This water-absorbing characteristic can be described and measured by equilibrium water content (EWC) as shown by Formula 1:

$$EWC(\%) = (Wgel - Wdry)/(Wgel) * 100 \qquad \text{Formula I:}$$

The EWC of embodiments of swellable (meth)acrylates of the present invention ranges between 5% and 70% in water, and may be pH dependent. EWC can also be measured after exposure to other liquids such as buffer (for example, phosphate buffer, at pH 7.4). In additional embodiments, the EWC (in water) of SAs of the present invention may range between 5% and 70%, between 5% and 50%, between 5% and 40%, between 10% and 40% between 5% and 35%, between 10% and 35% or between 15% and 35% in water. In further embodiments, after the swellable (meth)acrylates have been conjugated with peptides (SAP), the EWC of embodiments of SAPs of the present invention may be, for example, between 10-40% in water (data not shown).

Figure 1:
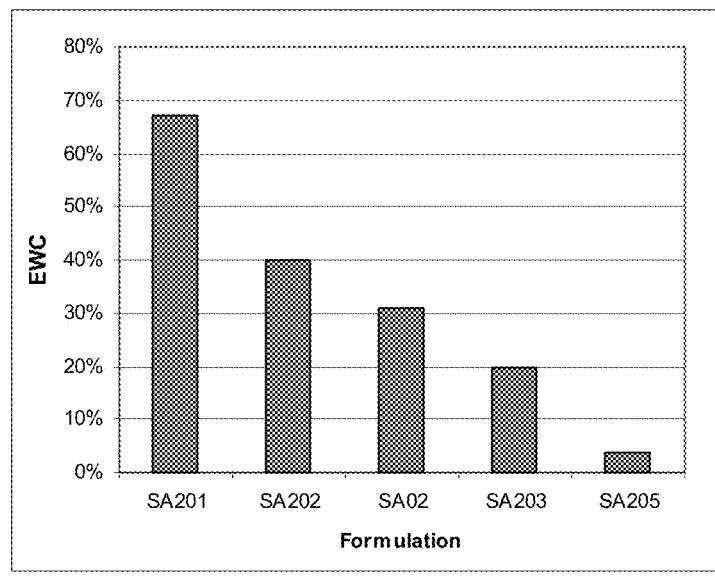
FIG. 1 is a graph illustrating the equilibrium water content of a selection of embodiments of swellable (meth)acrylate layers of the present invention.
Figure 2:
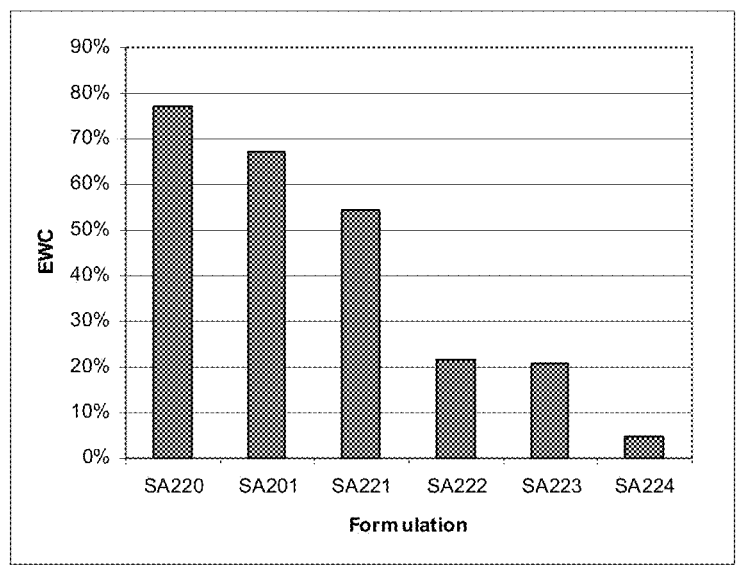
FIG. 2 is a graph illustrating the equilibrium water content of a selection of embodiments of swellable (meth)acrylate layers of the present invention having increasing concentrations of crosslinker.

FIG. 1 illustrates EWC measurements of a selection of embodiments of SAs when exposed to water. EWC measurements were greater in buffer solutions at pH 7.4 than in water (data not shown). Components of the SAs tested in FIG. 1 are reported in Table 1. IBA is isobutyl acrylate, a negative control. FIG. 2 illustrates EWC measurements of additional embodiments of SAs having increasing percentages of crosslinker FIG. 2 illustrates that as the percentage of crosslinker increases, the SA surfaces have a reduced equilibrium water content. More highly cross-linked SA surfaces become less swellable and harder.

In cell culture, prepared surfaces are exposed to an aqueous environment and the degree to which the surface absorbs water will affect the nature of the cell culture surface. For example, it might be that surfaces that absorb significant water, surfaces that are highly hydrogel-like, are more likely to delaminate from a substrate when exposed to an aqueous environment. Delamination has been described as a significant problem where hydrogels are used as cell culture surfaces. Some researchers have suggested that this problem of delamination can be solved by providing an interpenetrating network of polymers in the hydrogel structure (see, for example, *In Interpenetrating Networks*, Xie et al., American Chemical Society, Washington D.C., 1994, Vol. 239, 557).

In embodiments of the present invention, it may be that SA and SAP layers which have lower EWC measurements, and therefore do not absorb as much water, are better suited as materials for cell culture. This may be due to many factors. It may be that surfaces having a lower EWC do not delaminate as readily as surfaces having a higher EWC. This characteristic may be but one characteristic among many that lead to a successful cell culture coating, however. For example, subtle changes in the chemistry of the surface, the charge, the modulus, the EWC, or the hydrophobicity or hydrophilicity of the surface also contribute to the success of the surface as a cell culture surface. In embodiments, SA surfaces having an EWC below 40% may be particularly suitable for supporting hES cells in culture.

The present disclosure describes, inter alia, articles having synthetic surfaces for culturing undifferentiated stem cells. The surfaces may support proliferation and maintenance of undifferentiated stem cells in chemically defined media.

Cell Culture Article

Referring to FIG. 3A, a schematic diagram of a side view of an article 100 for culturing cells is shown. The article 100 includes a base material substrate 10 having a surface 15. A swellable (meth)acrylate or SA coating layer 20 is disposed on the surface 15 of the base material 10. While not shown, it will be understood that SA coating 20 may be disposed on a portion of base material 10. The base material 10 may be any material suitable for culturing cells, including a ceramic substance, a glass, a plastic, a polymer or co-polymer, any combinations thereof, or a coating of one material on another. The base material may be flat or shaped. Such base materials 10 include glass materials such as soda-lime glass, pyrex glass, vycor glass, quartz glass; silicon; plastics or polymers, including dendritic polymers, such as poly(vinyl chloride), poly(vinyl alcohol), poly(methyl methacrylate), poly(vinyl acetate-co-maleic anhydride), poly(dimethylsiloxane) monomethacrylate, cyclic olefin polymers, fluorocarbon polymers, polystyrenes, polypropylene, polyethyleneimine; copolymers such as poly(vinyl acetate-co-maleic anhydride), poly(styrene-co-maleic anhydride), poly(ethylene-co-acrylic acid) or derivatives of these or the like.

As used herein, "cyclic olefin copolymer" means a polymer formed from more than one monomer species, where at least one of the monomer species is a cyclic olefin monomer and at least one other monomer species is not a cyclic olefin monomer species. In many embodiments, cyclic olefin copolymers are formed from ethylene and norbonene monomers. Cyclic olefin copolymer resins are commercially available with trade name of TOPAS® from Boedeker Plastics, Inc.

Examples of articles 100 suitable for cell culture include single and multi-well plates, such as 6, 12, 96, 384, and 1536 well plates, jars, petri dishes, flasks, beakers, plates, roller bottles, slides, such as chambered and multichambered culture slides, tubes, cover slips, bags, membranes, hollow fibers, beads and microcarriers, cups, spinner bottles, perfusion chambers, bioreactors, CellSTACK® (Corning, Incorporated) and fermenters.

In embodiments, SAs may be polymerized from acrylate or methacrylate monomers and acrylate or methacrylate cross-linkers. The term "(meth)acrylate" refers to compounds containing acrylate or methacrylate groups. In embodiments, the (meth)acrylate monomers may include 2-hydroxyethyl methacrylate (HEMA), 2-carboxyethyl acrylate, 1-vinyl-2-pyrrolidone, di(ethylene glycol) ethyl ether methacrylate, acrylamide, ethylene glycol methyl ether methacrylate, 3-sulfopropyldimethyl-3-methacrylamidopropyl-ammonium inner salt and mixtures of these. Tetra(ethylene glycol) dimethacrylate may operate as a cross-linker. In embodiments, poplypeptides are not incorporated into the coating as cross-linkers. Representative swellable (meth)acrylates of the present invention are illustrated in Table 1.

SA coating 20 provides a surface 25 to which one or more polypeptides 70 may be conjugated. As used herein, "conjugated" means covalently bound. Covalent binding of polypeptide 70 to SA 20 may occur through a linker 80. In various embodiments, the SA surface 20 includes polymerized acrylate monomers; namely, hydroxyethyl methacrylate, 2-carboxyethylacrylate, and tetra(ethylene glycol) dimethacrylate. In numerous embodiments, the ratio (by volume) of hydroxyethyl methacrylate, 2-carboxyethylacrylate, and tetra(ethylene glycol)dimethacrylate is about 80/20/3 (v/v/v), respectively. In numerous embodiments, the SA is formulated using the following liquid aliquots of monomers (by volume): hydroxyethyl methacrylate (~60-90), 2-carboxyethylacrylate (~10-40), and tetra(ethylene glycol) dimethacrylate (~1-5), respectively. In numerous embodiments, the SA layer 20 consists essentially of polymerized hydroxyethyl methacrylate, 2-carboxyethylacrylate, and tetra(ethylene glycol)dimethacrylate monomers. In various embodiments, the SA layer 20 is substantially free of polypeptide crosslinkers.

In numerous embodiments, the SA is formulated using the monomers (by volume for liquid monomers or weight for solid monomers): Monomer X (80), 2-carboxyethylacrylate (20), and tetra(ethylene glycol)dimethacrylate (3). Monomer X is: Hydroxypropyl methacrylate, 2-Hydroxyethyl acrylate, 1-vinyl-2-pyrrolidone, Di(ethylene glycol) ethyl ether methacrylate, acrylamide, ethylene glycol methyl ether methacrylate or 3-sulfopropyldimethyl-3-methacrylamidopropyl-ammonium.

In various embodiments, polypeptide 70 includes a peptide or a polypeptide. For the purposes of this disclosure, peptide or polypeptide is an amino acid sequence that may be chemically synthesized or made by recombinant methods. However, for the purposes of this disclosure, peptide or polypeptide is a fragment of a protein, and not a complete protein. In addition, peptide or polypeptide is not isolated from an animal source. In embodiments, polypeptide 70 may include an amino acid sequence of XaanProGlnValThrArgGlyAspVal-PheThrMetPro (SEQ ID NO:1), a vitronectin peptide sequence where n is an integer from 0 to 3 and where Xaa may be any amino acid or may be, for example, lysine. The Xaa amino acid sequence may be a conjugation sequence as, for example, LysGlyGly or LysTyrGly, which provides a functional group, in the lysine amino acid, for conjugating the peptide to the SA surface. In addition, a peptide may be acetylated or amidated to provide stability and protect the small amino acid from cleavage. In additional embodiments, the peptide 70 includes an amino acid sequence of XaaGlyGlyAsnGlyGluProArgGlyAspThrTyrArgAlaTyr-NH$_2$ (SEQ ID NO:2), a BSP peptide sequence where Xaa may be any amino acid or may be, for example, lysine, Or, in embodiments, the peptide may be a combination of (SEQ ID NO:1) and (SEQ ID NO:2).

A linker or spacer 80, such as a repeating poly(ethylene glycol) linker or any other suitable linker, may be used to increase distance from polypeptide 70 to surface 25 of SA layer 20. All, some, or none of the polypeptides 70 may be conjugated to SA layer 20 via linkers 80. An acrylate chain which provides a conjugation group may also act as spacer for conjugated peptides.

Polypeptide 70 may be conjugated to the SA layer 20 at any density, preferably at a density suitable to support culture of undifferentiated stem cells, to form a swellable (meth)acrylate-peptide or SAP surface. Polypeptide 70 may be conjugated to SA layer 20 at a density of between about 1 pmol per mm$^2$ and about 50 pmol per mm$^2$ of surface 25 of swellable (meth)acrylate coating 20, which can be estimated by the area of surface 15 of base material substrate 10 that is coated in embodiments where surface 15 is uniformly coated by swellable (meth)acrylate layer 20. For example, the polypeptide may be present at a density of greater than 1 pmol/mm$^2$, greater than 5 pmol/mm$^2$, greater than 6 pmol/mm$^2$, greater than 7 pmol/mm$^2$, greater than 8 pmol/mm$^2$, greater than 9 pmol/mm$^2$, greater than 10 pmol/mm$^2$, greater than 12 pmol/mm$^2$, greater than 15 pmol/mm$^2$, or greater than 20 pmol/mm$^2$ of the surface 25 of the SA coating 20. It will be understood that the amount of polypeptide 70 present can vary depending on the composition of the SA layer 20, the thickness of the SA layer 20 and the nature of the polypeptide 70 itself. As discussed below in the Examples, higher densities of polypeptide 70 may be better able to support attachment and proliferation of undifferentiated stem cells in a chemically defined medium.

Acrylate and methacrylate monomers may be synthesized as known in the art or obtained from a commercial vendor, such as Polysciences, Inc., Sigma Aldrich, Inc., and Sartomer, Inc. Polypeptides 70 may be synthesized as known in the art (or alternatively produced through molecular biological techniques) or obtained from a commercial vendor, such as GenScript Corporation. Linkers 80 may be synthesized as known in the art or obtained from a commercial vendor, such as discrete polyethylene glycol (dPEG) linkers available from Quanta BioDesign, Ltd.

As shown in FIG. 3B, an intermediate layer 30 may be disposed between surface 15 of base material 10 and the SA coating 20. Intermediate layer 30 may be configured to improve binding of coating 20 to substrate 10, to facilitate monomer spreading, to render portions of the surface 10 that are uncoated cytophobic to encourage cell growth on coated areas, to provide a substrate compatible with a monomer or solvent where the monomer or solvent is incompatible with the base material 10, to provide topographical features if desired through, for example, patterned printing, or the like. For example, if substrate 10 is a glass substrate, it may be desirable to treat a surface of the glass substrate with an epoxy coating or a silane coating. For various polymer base materials 10 it may be desirable to provide an intermediate layer 30 of polyamide, polyimide, polypropylene, polyethylene, or poly(meth)acrylate. While not shown, it will be understood that SA coating 20 may be disposed on a portion of intermediate layer 30. It will be further understood that intermediate layer 30 may be disposed on a portion of base material 10.

In various embodiments, surface 15 of base material 10 is treated, either physically or chemically, to impart a desirable property or characteristic to the surface 15. For example, and as discussed below, surface 15 may be corona discharge treated or plasma treated. Examples of vacuum or atmospheric pressure plasma include RF and microwave plasmas both primary and secondary, dielectric barrier discharge, and corona discharge generated in molecular or mixed gases including air, oxygen, nitrogen, argon, carbon dioxide, nitrous oxide, or water vapor.

SA coating layer 20, whether disposed on an intermediate layer 30 or base material 10, preferably uniformly coats the underlying substrate. By "uniformly coated," it is meant that the layer 20 in a given area, for example a surface of a well of a culture plate, completely coats the area at a thickness of about 5 nm or greater. In embodiments, while the thickness of a uniformly coated surface may vary across the surface, there are no areas of the uniformly coated surfaces through which the underlying layer (either intermediate layer 30 or base material 10) is exposed. Cell responses across non-uniform surfaces tend to be more variable than cell responses across uniform surfaces.

SAP coating layer 20 may have any desirable thickness. In various embodiments, the average thickness of the coating layer 20 is less than about 10 micrometers. For example, the average thickness may be less than about 5 micrometers, less than about 2 micrometers, less than about 1 micrometers, less than about 0.5 micrometers, such as about 0.1 micrometers.

The polymer material forming SA layer 20 may be crosslinked to any suitable degree. Low degree of crosslinking may result in partial or complete swellable (meth)acrylate dissolution in water and lower polymerization reaction efficiency. In various embodiments, the crosslinking density of swellable (meth)acrylate layer 20 is between about 0.9% and about 9%.

Figure 4B:
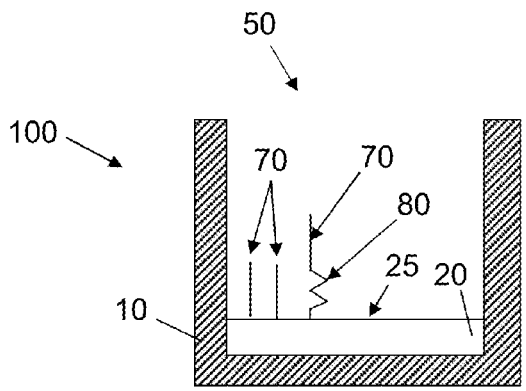
Figure 4C:
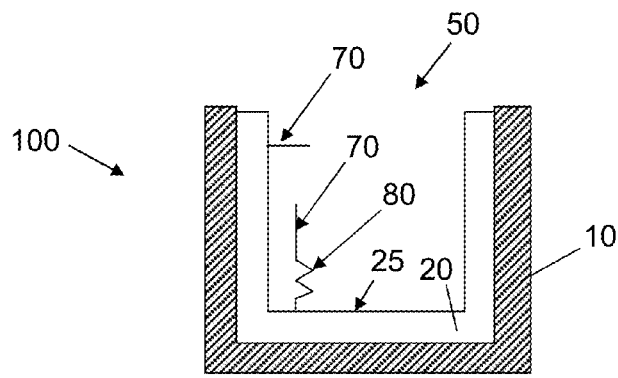

Article 100, in numerous embodiments, is cell culture ware having a well, such as a Petri dish, a multi-well plate, a flask, a beaker or other container having a well. Referring now to FIG. 4, article 100 formed from base material 10 may include one or more wells 50. Well 50 includes a sidewall 55 and a surface 15. Referring to FIG. 4B-C, a peptide-conjugated swellable (meth)acrylate (SAP) coating 20 may be disposed on surface 15 or sidewalls 55 (or, as discussed above with regard to FIG. 1 one or more intermediate layer 30 may be disposed between surface 15 or sidewall 55 and SA coating 20) or a portion thereof. As shown in FIG. 4C, 55 may be coated with SAP layer 20.

In various embodiments, article 100 includes a uniformly coated layer 20 having a surface 25 with an area greater than about 5 mm$^2$. When the area of the surface 15 is too small, reliable cell responses may not be readily observable because some cells, such as human embryonic stem cells, are seeded as colonies or clusters of cells (e.g., having a diameter of about 0.5 mm) and adequate surface is desirable to ensure attachment of sufficient numbers of colonies to produce a quantitative cell response. In numerous embodiments, an article 100 has a well 50 having a uniformly coated surface 15, where the surface 15 has an area greater than about 0.1 cm², greater than about 0.3 cm², greater than about 0.9 cm², or greater than about 1 cm².

2. Coating of Synthetic SA Layer

A synthetic SA layer may be disposed on a surface of a cell culture article via any known or future developed process. Preferably, the synthetic SA layer provides a uniform layer that does not delaminate during typical cell culture conditions. The synthetic SA surface may be associated with the base material substrate via covalent or non-covalent interactions. Examples of non-covalent interactions that may associate the synthetic SA surface with the substrate include chemical adsorption, hydrogen bonding, surface interpenetration, ionic bonding, van der Waals forces, hydrophobic interactions, dipole-dipole interactions, mechanical interlocking, and combinations thereof.

In numerous embodiments, monomers are deposited on a surface of a cell culture article and polymerized in situ. In such embodiments, the base material will be referred to herein as the "substrate" on which the synthetic SA material is deposited. Polymerization may be done in solution phase or in bulk phase.

As monomers may be viscous, it may be desirable to dilute the monomers in a suitable solvent to reduce viscosity prior to being dispensed on the surface. Reducing viscosity may allow for thinner and more uniform layers of the synthetic SA material to be formed. Preferably the solvent is compatible with the material forming the cell culture article and the monomers. It may be desirable to select a solvent that is non-toxic to the cells to be cultured and that does not interfere with the polymerization reaction. Alternatively, or in addition, selection of a solvent that can be substantially completely removed or removed to an extent that it is non-toxic or no longer interferes with polymerization may be desirable. In such circumstances, it may be desirable that the solvent be readily removable without harsh conditions, such as vacuum or extreme heat. Volatile solvents are examples of such readily removable solvents.

Some solvents that may be suitable in various situations for coating articles as described herein include ethanol, isopropanol, acetyl acetate, ethyl acetate, dimethylformamide (DMF), and dimethylsulfoxide (DMSO). As described in copending application Ser. No. 12/362,782, ethanol may be a particularly suitable solvent when it is desired to remove solvent prior to polymerization. However, in embodiments, other solvents including acetone, methanol, ethyl acetate, butanone, acetonitrile, 2-propanol and 2-butanol may be applicable.

The monomers may be diluted with solvent by any suitable amount to achieve the desired viscosity and monomer concentration. Generally the monomer compositions used according to the teachings presented herein contain between about 0.1% to about 99% monomer. By way of example, the monomer may be diluted with an ethanol or other solvent to provide a composition having between about 0.1% and about 50% monomer, or from about 0.1% to about 10% monomer by volume, or from about 0.1% to about 1% monomer by volume. The monomers may be diluted with solvent so that the SA layer achieves a desired thickness. As discussed above, if the deposited monomers are too thick, a non-uniform surface may result and the coating may likely de-laminate after contact with an aqueous medium.

In various embodiments, the synthetic SA layer is deposited on a surface of an intermediate layer that is associated with the base material via covalent or non-covalent interactions, either directly or via one or more additional intermediate layers (not shown). In such embodiments, the intermediate layer will be referred to herein as the "substrate" onto which the synthetic SA layer is deposited.

In various embodiments, the surface of the base material is treated. The surface may be treated to improve binding of the synthetic SA layer to the base material surface, to facilitate monomer spreading on the base material surface, or the like. Of course, the base material may be treated for similar purposes with regard to an intermediate layer. In various embodiments, the surface is plasma treated. High surface energy obtainable from such treatments may facilitate monomer spreading and uniform coating.

In addition to the monomers that form the SA layer, a composition forming the layer may include one or more additional compounds such as surfactants, wetting agents, photoinitiators, thermal initiators, catalysts and activators.

Any suitable polymerization initiator may be employed. One of skill in the art will readily be able to select a suitable initiator, e.g. a radical initiator or a cationic initiator, suitable for use with the monomers. In various embodiments, UV light is used to generate free radical monomers to initiate chain polymerization.

Any suitable initiator may be used. Examples of polymerization initiators include organic peroxides, azo compounds, quinones, nitroso compounds, acyl halides, hydrazones, mercapto compounds, pyrylium compounds, imidazoles, chlorotriazines, benzoin, benzoin alkyl ethers, diketones, phenones, or mixtures thereof. Examples of suitable commercially available, ultraviolet-activated and visible light-activated photoinitiators have tradenames such as IRGACURE 651, IRGACURE 184, IRGACURE 369, IRGACURE 819, DAROCUR 4265 and DAROCUR 1173 commercially available from Ciba Specialty Chemicals, Tarrytown, N.Y. and LUCIRIN TPO and LUCIRIN TPO-L commercially available from BASF (Charlotte, N.C.)

A photosensitizer may also be included in a suitable initiator system. Representative photosensitizers have carbonyl groups or tertiary amino groups or mixtures thereof. Photosensitizers having a carbonyl groups include benzophenone, acetophenone, benzil, benzaldehyde, o-chlorobenzaldehyde, xanthone, thioxanthone, 9,10-anthraquinone, and other aromatic ketones. Photosensitizers having tertiary amines include methyldiethanolamine, ethyldiethanolamine, triethanolamine, phenylmethyl-ethanolamine, and dimethylaminoethylbenzoate. Commercially available photosensitizers include QUANTICURE ITX, QUANTICURE QTX, QUANTICURE PTX, QUANTICURE EPD from Biddle Sawyer Corp.

In general, the amount of photosensitizer or photoinitiator system may vary from about 0.01 to 10% by weight.

Examples of cationic initiators include salts of onium cations, such as arylsulfonium salts, as well as organometallic salts such as ion arene systems.

In various embodiments where the monomers are diluted in solvent before being deposited on the substrate surface, the solvent is removed prior to polymerizing. The solvent may be removed by any suitable mechanism or process. As described in copending application Ser. No. 12/362,782, it has been found that removal of substantially all of the solvent prior to curing, allows for better control of curing kinetics and the amount of monomer converted. When conversion rates of the monomers are increased, waste generation and cytotoxicity are reduced. Using these methods, the resulting SA layer forms a network, but not an interpenetrating network.

To form the synthetic SA surface, the monomers are polymerized. Whether polymerized in bulk phase (substantially solvent free) or solvent phase, the monomers are polymerized via an appropriate initiation mechanism. Many of such mechanisms are known in the art. For example, temperature may be increased to activate a thermal initiator, photoinitiators may be activated by exposure to appropriate wavelength of light, or the like. According to numerous embodiments, the monomer or monomer mixture is cured using UV light. The curing preferably occurs under inert gas protection, such as nitrogen protection, to prevent oxygen inhibition. Suitable UV light combined with gas protection may increase polymer conversion, insure coating integrity and reduce cytotoxicity.

The cured synthetic SA layer may be washed with solvent one or more times to remove impurities such as unreacted monomers or low molecular weight polymer species. In various embodiments, the layer is washed with ethanol or an ethanol-water solution, e.g. 70% ethanol, greater than 90% ethanol, greater than 95% ethanol or greater than about 99% ethanol. Washing with a 70% ethanol solvent may not only serve to remove impurities, which may be cytotoxic, but also can serve to sterilize the surface prior to incubation with cells.

A polypeptide may be conjugated to the polymerized SA layer via any suitable technique to form a SAP surface. A polypeptide may be conjugated to a polymerized SA layer 20 via an amino terminal amino acid, a carboxy terminal amino acid, or an internal amino acid. One suitable technique involves 1-ethyl-3-[3-dimethylaminopropyl]carbodiimide hydrochloride (EDC)/N-hydroxysuccinimide (NHS) chemistry, as generally known in the art. EDC and NHS or N-hydroxysulfosuccinimide (sulfo-NHS) can react with carboxyl groups of the SA layer to produce amine reactive NHS esters. In embodiments of the present invention, the incorporation of a monomer in the SA layer having a carboxyl group for conjugation with peptides is important. EDC reacts with a carboxyl group of the SA layer to produce an amine-reactive O-acylisourea intermediate that is susceptible to hydrolysis. The addition of NHS or sulfo-NHS stabilizes the amine-reactive O-acylisourea intermediate by converting it to an amine reactive NHS or sulfo-NHS ester, allowing for two step procedures. Following activation of the SA layer, the polypeptide may then be added and the terminal amine of the polypeptide can react with the amine reactive ester to form a stable amide bond, thus conjugating the polypeptide to the SA layer. When EDC/NHS chemistry is employed to conjugate polypeptide to SA layer, the N-terminal amino acid is preferably an amine containing amino acid such as lysine, ornithine, diaminobutyric acid, or diaminoproprionic acid. Of course, any acceptable nucleophile may be employed, such as hydroxylamines, hydrazines, hydroxyls, and the like.

EDC/NHS chemistry results in a zero length crosslinking of polypeptide 70 to SA layer 20. Linkers or spacers, such as poly(ethylene glycol) linkers (e.g., available from Quanta BioDesign, Ltd.) with a terminal amine may be added to the N-terminal amino acid of polypeptide 70. When adding a linker to the N-terminal amino acid, the linker is preferably a N-PG-amido-PEG$_X$-acid where PG is a protecting group such as the Fmoc group, the BOC group, the CBZ group or any other group amenable to peptide synthesis and X is 2, 4, 6, 8, 12, 24 or any other discrete PEG which may be available.

In various embodiments, a 1 µM-2500 µM polypeptide fluid composition, such as a solution, suspension, or the like, is contacted with an activated SA layer to conjugate the polypeptide. For example the polypeptide concentration may be between about 100 µM and about 2000 µM, between about 500 µM and about 1500 µM, or about 1000 µM. It will be understood that the volume of the polypeptide composition and the concentration may be varied to achieve a desired density of polypeptide conjugated to the SA layer. In general, a peptide density of between 1 and 50 pmol/mm$^2$. In some embodiments, a peptide density of between 3-8 pmol/mm$^2$ may provide a surface that is comparable to known cell culture surfaces such as Matrigel®.

3. Sterilization of Synthetic SAP Layer

Commercially viable cell culture products need to be sterile. Sterilization can occur by various methods including assembly of sterile components under aseptic conditions (in an aseptic manufacturing facility) or terminal sterilization, i.e. exposure to sterilizing agents such as UV light, chemicals (ethanol, ethylene oxide) or ionizing radiation (gamma or electron) after assembly. Terminal sterilization is more desirable than aseptic manufacturing because it is very expensive to implement aseptic manufacturing on a large scale and it is prone to ongoing contamination issues. Radiation in the gamma frequency range (>3×10 19 Hz) penetrates packaging materials and can be applied on large scale at ambient temperatures. Electron beam irradiation can be accomplished in seconds to a few minutes because it delivers a higher dose of radiation than gamma, allowing less oxygen to permeate the materials which may cause less damage than gamma treatments. Gamma irradiation is typically used for sterilizing cell culture ware after packaging. Depending upon the bio-burden of each process and product, a sterility assurance level (SAL) of 10-3 is typically expected for cell culture products. However, E-beam or EB treatments also have advantages and are also contemplated in embodiments of the present invention.

Peptides, such as SEQ ID NO:1 and SEQ ID NO:2 are short segments of macromolecular proteins and are known to be damaged by irradiation techniques. Most irradiation based sterilization techniques result in fragmentation of these small molecular entities and render them ineffective in facilitation bio-specific cell attachment. Therefore, it is challenging for peptide containing cell culture surface products to be manufactured, packaged, sterilized, stored and distributed in the normal stream of commerce. Surprisingly, in embodiments of the present invention, swellable (meth)acrylate surfaces conjugated to a peptide sequence identified as SEQ ID NO:1 undergo irradiation sterilization without losing function (See FIG. 7). Other peptides conjugated to embodiments of the swellable (meth)acrylate surfaces of the present invention lost function after irradiation sterilization.

4. Incubating Cells on Synthetic SAP Layer

A cell culture article having a SAP layer as described above may be seeded with cells. The cells may be of any cell type. For example, the cells may be connective tissue cells, epithelial and endothelial cells, hepatocytes, skeletal or smooth muscle cells, heart muscle cells, intestinal cells, kidney cells, or cells from other organs, stem cells, islet cells, blood vessel cells, lymphocytes, cancer cells, or the like. The cells may be mammalian cells, preferably human cells, but may also be non-mammalian cells such as bacterial, yeast, or plant cells.

In numerous embodiments, the cells are stem cells which, as generally understood in the art, refer to cells that have the ability to continuously divide (self-renewal) and that are capable of differentiating into a diverse range of specialized cells. In some embodiments, the stem cells are multipotent, totipotent, or pluripotent stem cells that may be isolated from an organ or tissue of a subject. Such cells are capable of giving rise to a fully differentiated or mature cell types. A stem cell may be a bone marrow-derived stem cell, autologous or otherwise, a neuronal stem cell, or an embryonic stem cell. A stem cell may be nestin positive. A stem cell may be a hematopoeietic stem cell. A stem cell may be a multi-lineage cell derived from epithelial and adipose tissues, umbilical cord blood, liver, brain or other organ. In various embodiments, the stem cells are pluripotent stem cells, such as pluripotent embryonic stem cells isolated from a mammal. Suitable mammals may include rodents such as mice or rats, primates including human and non-human primates. These cells have applications in cell therapy, tissue repair, drug development, and the study of developmental biology. Many of these cell lines require the use of mouse or human feeder cells to inhibit differentiation. Tumor extract matrices are available such as Matrigel® (mouse sarcoma-derived commercial product containing a mixture of laminin, collagen IV, entactin, heparin sulfate proteoglycan and other proteins, available from BD Biosciences, Franklin Lakes, N.J.

Because human embryonic stem cells (hESC) have the ability to grown continually in culture in an undifferentiated state, the hESC for use in this invention may be obtained from an established cell line. Examples of human embryonic stem cell lines that have been established include, but are not limited to, H1, H7, H9, H13 or H14 (available from WiCell established by the University of Wisconsin) (Thompson (1998) Science 282:1145); hESBGN-01, hESBGN-02, hES-BGN-03 (BresaGen, Inc., Athens, Ga.); HES-1, HES-2, HES-3, HES-4, HES-5, HES-6 (from ES Cell International, Inc., Singapore); HSF-1, HSF-6 (from University of California at San Francisco); 13, 13.2, 13.3, 14, 16, 16.2, J 3, J 3.2 (derived at the Technion-Israel Institute of Technology, Haifa, Israel); UCSF-1 and UCSF-2 (Genbacev et al., Fertil. Steril. 83(5):1517-29, 2005); lines HUES 1-17 (Cowan et al., NEJM 350(13):1353-56, 2004); and line ACT-14 (Klimanskaya et al., Lancet, 365(9471):1636-41, 2005). Embryonic stem cells used in the invention may also be obtained directly from primary embryonic tissue. Typically this is done using frozen in vitro fertilized eggs at the blastocyst stage, which would otherwise be discarded.

Other sources of pluripotent stem cells include induced primate pluripotent stem (iPS) cells. iPS cells refer to cells, obtained from a juvenile or adult mammal, such as a human, that are genetically modified, e.g., by transfection with one or more appropriate vectors, such that they are reprogrammed to attain the phenotype of a pluripotent stem cell such as an hESC. Phenotypic traits attained by these reprogrammed cells include morphology resembling stem cells isolated from a blastocyst as well as surface antigen expression, gene expression and telomerase activity resembling blastocyst derived embryonic stem cells. The iPS cells typically have the ability to differentiate into at least one cell type from each of the primary germ layers: ectoderm, endoderm and mesoderm. The iPS cells, like hESC, also form teratomas when injected into immuno-deficient mice, e.g., SCID mice. (Takahashi et al., (2007) Cell 131(5):861; Yu et al., (2007) Science 318: 5858).

Stem cells, including embryonic stem cells (ESCs) and human embryonic stem cells (hESCs) are difficult to culture, especially in an undifferentiated, pluripotent state. Controlling these cells in culture, maintaining them in an undifferentiated state and subsequently directing them to differentiate in a reliable and reproducible manner has been challenging. Stem cells have required naturally derived components to survive in culture, in or on the cell culture surface (for example, Matrigel®) or in the medium (for example serum or conditioned media), or both. Spontaneous differentiation often occurs in culture, presumably resulting from soluble factors, cell-cell contact, and/or cell-matrix signaling. All of these factors are unpredictable when these cells are cultured in the presence of factors that are of animal origin, resulting in cultures that are difficult to predict and control. Protein products from natural sources show batch to batch variability where both compositional and functional differences are found between batches. For example, exposure of ESCs or hESCs to xenogenic products introduces the risk of contamination by adventitious infectious agents. Moreover, ESCs cultured with animal derived substrates or serum products could take up and express neu5Gc (a non-human sialic acid) thereby causing a significant risk of immune reaction in a transplantation. Purely synthetic surfaces for stem cell culture, which enable the culture of undifferentiated stem cells in defined media, are desirable.

Prior to seeding cells, the cells may be harvested and suspended in a suitable medium, such as a growth medium in which the cells are to be cultured once seeded onto the surface. For example, the cells may be suspended in and cultured in a serum-containing medium, a conditioned medium, or a chemically-defined medium. As used herein, "chemically-defined medium" means cell culture media that contains no components of unknown composition. Chemically defined media may, in various embodiments, contain no proteins, hydroxylates, or peptides of unknown composition. In embodiments of the present invention, chemically defined media does not contain animal-derived ingredients. Undefined animal derived ingredients such as fetal bovine serum, cell extracts such as those found in "conditioned" media, or animal derived ingredients such as bovine serum albumin are not acceptable constituents of a chemically defined medium in embodiments of the present invention. In some embodiments, chemically defined media contains polypeptides or proteins of known composition. These polypeptides or proteins may be synthesized or recombinant. For example, chemically defined media may contain recombinant growth hormones. Because all components of chemically defined media have a known chemical structure and are introduced to the media in known quantities, variability in culture conditions and thus cell response can be reduced, increasing reproducibility. In addition, the possibility of contamination from undefined and animal-derived constituents is removed. Further, the ability to scale up is made easier due, at least in part, to the factors discussed above. There are chemically defined cell culture media commercially available from, for example, Invitrogen (Invitrogen Corporation, 1600 Faraday Avenue, PO Box 6482, Carlsbad, Calif. 92008) as STEM PRO, a fully serum- and feeder-free (SFM) specially formulated from the growth and expansion of embryonic stem cells, and Stem Cell Technologies, Inc. as mTeSR™1 maintenance media for human embryonic stem cells.

One or more growth or other factors may be added to the medium in which cells are incubated with the synthetic SAP layer. The factors may facilitate cellular proliferation, adhesion, self-renewal, differentiation, or the like. Examples of factors that may be added to or included in the medium include muscle morphogenic factor (MMP), vascular endothelium growth factor (VEGF), interleukins, nerve growth factor (NGF), erythropoietin, platelet derived growth factor (PDGF), epidermal growth factor (EGF), activin (ACT), hematopoietic growth factors, retinoic acid (RA), interferons, fibroblastic growth factors, such as basic fibroblast growth factor (bFGF), bone morphogenetic protein (BMP), peptide growth factors, heparin binding growth factor (HBGF), hepatocyte growth factor, tumor necrosis factors, insulin-like growth factors (IGF) I and II, transforming growth factors, such as transforming growth factor-β1 (TGFβ1), and colony stimulating factors.

The cells may be seeded at any suitable concentration. Typically, the cells are seeded at about 10,000 cells/cm$^2$ of substrate to about 500,000 cells/cm$^2$. For example, cells may be seeded at about 50,000 cells/cm$^2$ of substrate to about 150,000 cells/cm$^2$. However, higher and lower concentrations may readily be used. The incubation time and conditions, such as temperature, $CO_2$ and $O_2$ levels, growth medium, and the like, will depend on the nature of the cells being cultured and can be readily modified. The amount of time that the cells are incubated on the surface may vary depending on the cell response desired.

The cultured cells may be used for any suitable purpose, including (i) obtaining sufficient amounts of undifferentiated stem cells cultured on a synthetic surface in a chemically defined medium for use in investigational studies or for developing therapeutic uses, (ii) for investigational studies of the cells in culture, (iii) for developing therapeutic uses, (iv) for therapeutic purposes, (v) for studying gene expression, e.g. by creating cDNA libraries, and (vi) for studying drug and toxicity screening.

In the following, non-limiting examples are presented, which describe various embodiments of the articles and methods discussed above.

EXAMPLES

Example 1

Identification of Synthetic Surfaces for Culturing Undifferentiated Human Embryonic Stem Cells in Chemically Defined Medium 1. Coating Preparation—96 Well Plates SA coating surfaces were prepared from UV polymerizable monomers and include a hydrophilic monomer, a carboxyl group containing monomer, and a crosslinking monomer. Table 1 shows the combination of swellable (meth) acrylate monomers employed in embodiments of the present invention.

TABLE 1

| Swellable (meth)acrylate No. | Hydrophilic Monomer (vol. %) | Carboxyl group containing monomer (vol. %) | Crosslinking monomer (vol. %) |
|---|---|---|---|
| SA02 | hydroxyethyl methacrylate (80) 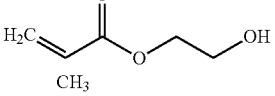 | 2-carboxyethyl acrylate (20) 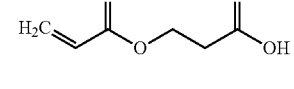 | Tetra(ethylene glycol) dimethacrylate (3) 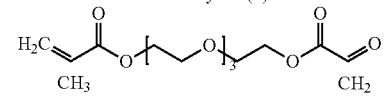 |
| SA220 | 1-vinyl-2-pyrrolidone(80) 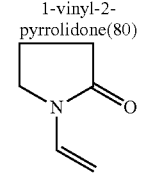 | 2-carboxyethyl acrylate (20) 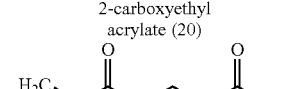 | Tetra(ethylene glycol) diacrylate (1) 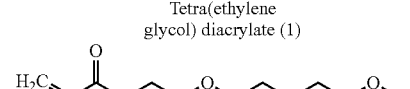 |
| SA201 | 1-vinyl-2-pyrrolidone(80) | 2-carboxyethyl acrylate (20) | Tetra(ethylene glycol) diacrylate (3) |
| SA221 | 1-vinyl-2-pyrrolidone(70) | 2-carboxyethyl acrylate (20) | Tetra(ethylene glycol) diacrylate (10) |
| SA222 | 1-vinyl-2-pyrrolidone(50) | 2-carboxyethyl acrylate (20) | Tetra(ethylene glycol) diacrylate (30) |
| SA223 | 1-vinyl-2-pyrrolidone(30) | 2-carboxyethyl acrylate (20) | Tetra(ethylene glycol) diacrylate (50) |
| SA224 |  | 2-carboxyethyl acrylate (20) | Tetra(ethylene glycol) diacrylate (80) |
| SA202 | 2-Hydroxyethyl acrylate(80) 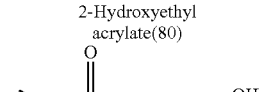 | 2-carboxyethyl acrylate (20) | Tetra(ethylene glycol) diacrylate (3) |
| SA203 | hydroxyethyl methacrylate (80) | 2-carboxyethyl acrylate (20) | Tetra(ethylene glycol) diacrylate (3) |
| SA205 | Isobutyl acrylate (80) 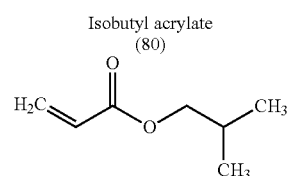 | 2-carboxyethyl acrylate (20) | Tetra(ethylene glycol) diacrylate (3) |

Briefly, the monomers were diluted in ethanol to the concentration of 0.1% by volume, and Durocur 1173 (3% volume/monomer volume) and Irgacure 819 (0.1% volume/monomer volume) photoinitiators was added. The diluted monomer formulations were added to a plasma treated appropriately sized cell culture vessel format (e.g. 96- or 6-well plates) cyclic olefin copolymer (provided by Corning Life Science Development group). An appropriate amount of the mixture was added to form a coating of an appropriate thickness. For example, a coating thickness below 2 microns is helpful for stability of the coating during conjugation reactions and cell culture assays. For example, a volume of 2 µL-5 µL was added to 96 well plates to form the appropriate coating thickness using BioTek Precision Pipetting System.

Each well received a predetermined swellable (meth)acrylate formulation, with some wells being coated with MATRIGEL® as a positive control. Unless stated otherwise, the resulting SA coatings had an average thickness of about 0.1 micrometers. For the wells coated with SA formulations, the ethanol solvent was removed by evaporation at room temperature for 3 hr in fume hood. After the solvent was removed, the coatings were cured with 13 mW/cm$^2$ pulsed (100 Hz) UV light (Xenon RC-801) for 1 min in N$_2$ purged box (with fused silica window).

2. Coating Preparation—Larger Format Surfaces

The formulations and general methods for the synthesis of peptide acrylate coatings (as described above) are universal for all formats. To apply these formulations to larger format cell culture surfaces such as 6-well plates and T-75 flasks, a spin coating process was used. This spin coating process allowed for application of more viscous materials to the surface. For example, in embodiments, a dispensing technique requires that the solution of monomers be diluted in a solvent to allow the dispensed liquid to disperse across a surface. For dispensing techniques, a 1% monomer solution diluted in a 99% ethanol solution may be an appropriate dilution. However, in embodiments, spin coating techniques allow for a range of between 0.1%-99.9% monomer in solvent to be applied to a surface. In embodiments, using a spin coating technique, the percent of acrylate monomers in the ethanol carrier solvent can be varied to achieve a wide range of desired coating thickness. In addition, spin coating allows these coatings to be applied to larger format surfaces, including 6-well plates, T175 flasks or larger flask formats. To deliver uniform coatings without any defects associated with delaminations, air pockets or other defects, the parameters of spin speed and spin time were modulated to ensure reproducible application of these coatings.

A Zenor ZF-16-188 (Zeon Chemicals) film is placed in an O$_2$ microwave plasma for 13 seconds (Plasmatic Systems). After treatment the thin film was fitted into a vacuum porous chuck of the spin coating axle. The chuck was then secured on the spin coater from Laurell Technologies (W5650-15NPP/AS/10K). Approximately 3 ml of the acrylate formulation was manually dispensed on the thin film. Table 3 shows the parameters that were used to enable the coating to spread evenly on a 5 inch by 5 inch film. After the acrylate formulation is applied to the film, and the solvent is evaporated, the film is placed in the UV chamber, purged with Nitrogen and cured for 1 minute. The spun coated films were then laminated (via an in-mold labeling process) into 6-well plates and T-75 flasks.

TABLE 2

| Acrylate Concentration (%) | Spin Speed (rpm) | Spin Time (sec.) |
|---|---|---|
| 5 | 1000 | 30 |
| 10 | 5000 | 30 |
| 15 | 3000 | 15 |
| 90 | 6000 | 30 |
| 100 | 5000 | 30 |

3. Polypeptide Conjugation to Swellable (Meth)Acrylate Surface

In a series of experiments designed to evaluate polypeptide conjugation to the swellable (meth)acrylate coatings prepared as described above, a polypeptide (ArgGlyGlySerAspProIleTyrLys (SEQ ID NO:3)/Rhod-GlyArgGlyAspSerProIleIleLys (SEQ ID NO:4)) was conjugated to a swellable (meth)acrylate coating of Formulation SA02 (see Tables 1 and 2) using 1-ethyl-3-[3-dimethylaminopropyl]carbodiimide hydrochloride (EDC)/N-hydroxysuccinimide (NHS) chemistry. Briefly, 50 µL of 0.1 M EDC and 0.05 M NHS solution in DMF were dispensed into a well of 96-well cyclic olefin plate coated with swellable (meth)acrylate formulation. The activation of carboxyl groups was allowed to proceed for 1-1.5 h and then the activating solution was aspirated. Immediately after that, 50 µL of polypeptide solution in 25 mM phosphate buffer pH 7.4 were dispensed into the well and reaction between well surface NHS esters and peptide primary amine groups was carried out at ambient condition for 1.5 h. Then, peptide solution was aspirated. After peptide conjugation the remaining NHS esters on the coating were blocked with 1M, pH 8.1 solution of ethanolamine or aminopropyl morpholine and the wells were washed with phosphate buffer, 1% SDS solution, and finally deionized water. Fluorescence was quantified using a Tecan microarray scanner. Alternatively, the polypeptides were quantified with the QuantiPro BCA assay kit available from Sigma-Aldrich. The peptide solution contained 1000 µM, 100 µM, 50 µM, 10 µM, 5 µM, 1 µM, or 0 µM total peptide.

TABLE 3

Peptides conjugated to swellable (meth)acrylate surfaces and tested in hESC culture

| Peptide ID | Peptide sequence |
|---|---|
| VN | XaanProGlnValThrArgGlyAspValPheThrMetPro (SEQ ID NO: 1) |
| BSP | XaaGlyGlyAsnGlyGluProArgGlyAspThrTyrArgAlaTyr (SEQ ID NO: 2) |
| 3 | ArgGlyGlySerAspProIleTyrLys (SEQ ID NO: 3) |
| 4 | Rhod-GlyArgGlyAspSerProIleIleLys (SEQ ID NO: 4) |
| VN-2 | LysGlyGlyProGlnValThrArgGlyAspValPheThrMetPro (SEQ ID NO: 5) |
| BSP-2 | LysGlyGlyAsnGlyGluProArgGlyAspThrTyrArgAlaTyr (SEQ ID NO: 6) |
| VN-3 | XaaGlyGlyProGlnValThrArgGlyAspValPheThrMetPro (SEQ ID NO: 7) |

Figure 5:
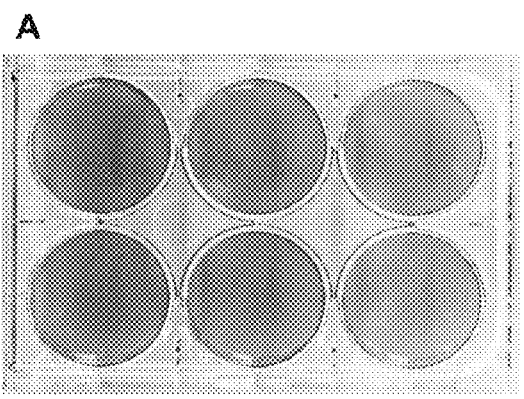
FIG. 5A is a photograph of a 6-well plate coated with an embodiment of the synthetic swellable (meth)acrylate coating of the present invention.
FIG. 5B is an absorbance image of two wells of a crystal violet stained 6-well plate showing uniform coating across the well.
Figure 5:
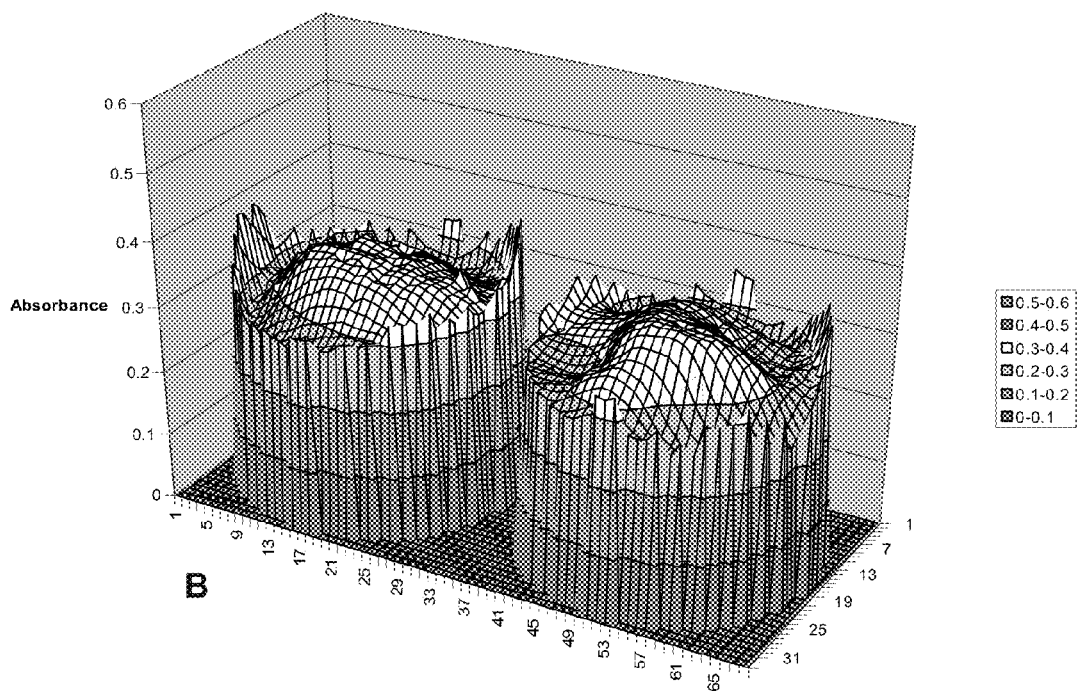

To show uniformity of the coatings, The SAP coated plates (spin coated) were stained with a 1:5 dilution of Gram Crystal Violet Dye (Becton, Dickenson, catalog number 212525) in water for 2 minutes at room temperature. After incubation the surface was rinsed three times with de-ionized water. An absorbance reading at 570 nm was taken on a plate reader (Perkin Elmer Victor3 1420 Multichannel Counter). FIG. 5A is a photograph of a crystal violet stained 6-well plate coated with an embodiment of the synthetic swellable (meth)acrylate coating of the present invention (prior to peptide conjugation). FIG. 5B is an absorbance image of two wells of a crystal violet stained 6-well plate showing uniform coating across the well.

4. Sterilization

Figure 6:
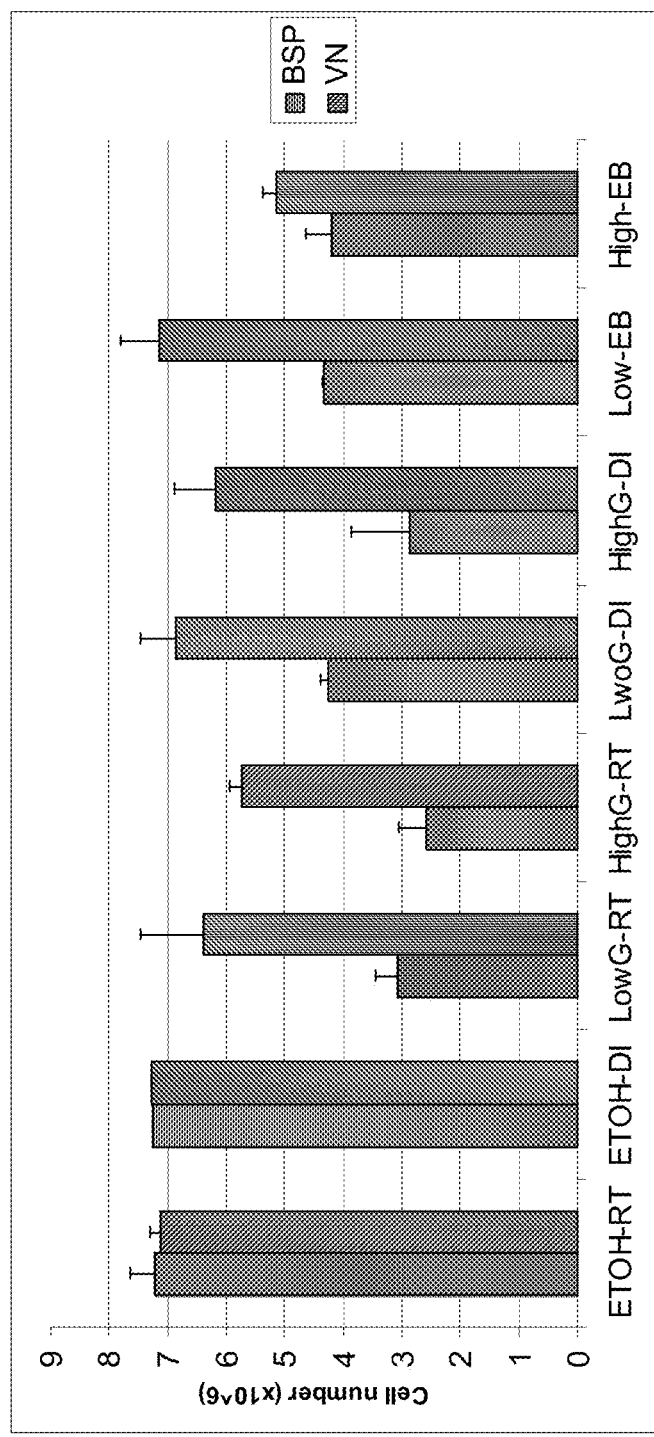
FIG. 6 is a graph showing the effects of irradiation sterilization techniques on different embodiments of coated surfaces of the present invention.

Spun-coated SAP plates (6-well plates) were packaged in the absence of air in aluminum pouches. The packaged plates were either placed in boxes at room temperature or over layers of dry ice. The packaged plates were then sent to a sterilization service vendor (for gamma sterilization STERIS of Chester, N.Y., for e-beam sterilization, STERIS of Libertyville Ill.). FIG. 6 is a graph illustrating the effects of gamma and e-beam irradiation sterilization treatments compared to ethanol sterilization on cell response for embodiments of the SAP surfaces of the present invention. LowG and HighG represents substrates treated with low dose (10-15 kGy) or high dose (15-25 kGy) Gamma irradiation respectively. Low-EB and High EB represent substrates treated with low (15-25 kGy) or high (25-40 kGy) dose electron beam radiation respectively. RT and DI represent samples stored at room temperature or in dry ice respectively. In addition to Matrigel® coated plates, swellable (meth)acrylate coated plates sterilized with 70% ethanol (ETOH) just prior to use were also used as controls to assess the impact of the sterilization.

The sterilized samples were assessed for H7 hES cell adhesion and proliferation after 4 or 5 days of culture. The cell number was established using an automated cell counter WiCell. FIG. 6 illustrates SAP surfaces (SA02 in Table 1) where the peptide is a BSP sequence (SAP-BSP) (SEQ ID NO:2 or SEQ ID NO:6) and where the peptide is a vitronectin (VN) sequence (SAP-VN) (SEQ ID NO:1 or SEQ ID NO:5) While both SAP surfaces provided appropriate surfaces for H7 hES cell adhesion and proliferation after EtOH sterilization, the SAP-VN surface retained its adhesive characteristics after low and high e-beam (EB) and gamma (G) sterilization treatments, when the treatments were provided at room temperature (RT) and on dry ice (DI). The SAP-BSP surface was damaged by the sterilization treatments.

Figure 7:
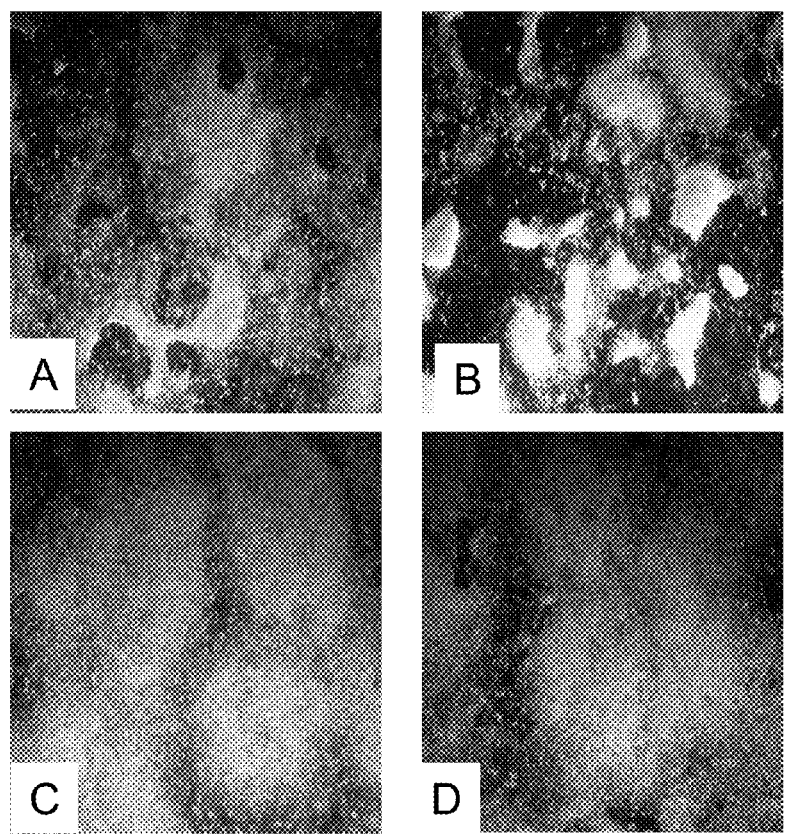
FIG. 7 A-D are phase contrast images of cells growing on embodiments of coated surfaces of the present invention after sterilization treatments.

FIG. 7A-D shows photomicrographs of cells cultured on gamma sterilized SAP BSP or VN surfaces for 5 days. FIG. 7A shows cells growing on a SAP surface conjugated with the BSP peptide sequence (SEQ ID NO:2 or SEQ ID NO:6) after 10-18 kGy gamma irradiation sterilization treatment (at room temperature). FIG. 7B shows cells growing on a SAP surface conjugated with the BSP peptide sequence (SEQ ID NO:2 or SEQ ID NO:6) after 15-25 kGy gamma irradiation sterilization treatment (at room temperature). FIG. 7C shows cells growing on a SAP surface conjugated the VN peptide sequence (SEQ ID NO:1 or SEQ ID NO:5) after 10-18 kGy gamma irradiation sterilization treatment (at room temperature). FIG. 7D shows cells growing on a SAP surface conjugated the VN peptide sequence (SEQ ID NO:1 or SEQ ID NO:5) after 15-25 kGy gamma irradiation sterilization treatment (at room temperature). The BSP conjugated coatings were more sensitive to the gamma and E-beam methods as evidenced by the reduced cell number observed only on the BSP conjugated surfaces (FIG. 6). The reduction in cell number on BSP conjugated acrylate surfaces was also associated with a cell colony morphology that was highly cystic (FIG. 7). This change in colony morphology may be associated with loss of cell surface markers for un-differentiated hES cells.

5. Adhesion of HT1080 Cells on SWAP Surfaces

To evaluate the ability of the VN conjugated acrylate surfaces (SEQ ID NO:1 or SEQ ID NO:5) to support cell adhesion and proliferation, an adhesion assay using HT1080 cells was carried out. Briefly, control wells were coated with Fibronectin (FN, 5 μg/mL, Sigma-Aldrich) for 1 hour at room temperature. All wells were blocked with 1% BSA in PBS for 1 hour at 37° C. Wells were washed briefly with PBS before incubation with 0.1% BSA in IMDM prior to cell seeding. HT-1080 human fibrosarcoma cells (ATCC number: CCL-121) were grown in IMDM (Lonza) with 10% FBS (Lonza) to 90% confluency at standard cell culture conditions. Cells were trypsinized and allowed to recover in IMDM with 10% FBS for 30 minutes at 37° C., 5% $CO_2$. After recovery, cells were washed and resuspended in 0.1% BSA in IMDM and seeded on peptide-conjugated acrylate coated plates and FN coated control wells at a density of 30,000 cells/well. Cell adhesion was allowed to take place for 1 hour at standard cell culture conditions. The media was aspirated from the wells and adherent cells were fixed and stained in 50 μL of 0.2% crystal violet in 20% methanol for 8 minutes at room temperature. Cellular absorption of crystal violet was quantified through addition of 1% SDS in $H_2O$ for 5 minutes prior to absorbance measurement at 570 nm.

Figure 8:
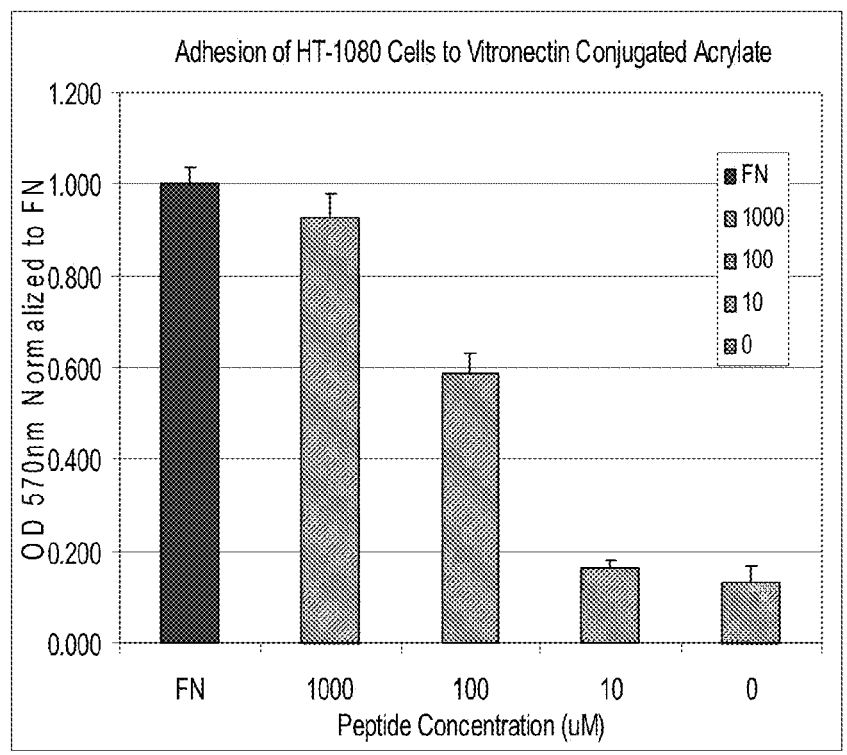
FIG. 8 is a graph showing the dose dependence of adhesion of cells to embodiments of coated surfaces of the present invention.

FIG. 8 is a graph illustrating adhesion of HT1080 cells on SAP-VN surfaces where the peptide is fibronectin protein (FN) or a vitronectin sequence (SEQ ID NO:1 or SEQ ID NO:5) present in varying concentrations. Fibronectin coated wells were the positive control. FIG. 8 illustrates that HT1080 cells adhere to embodiments of the SAP surfaces of the present invention in a concentration dependent manner.

6. Growth Medium

Figure 9:
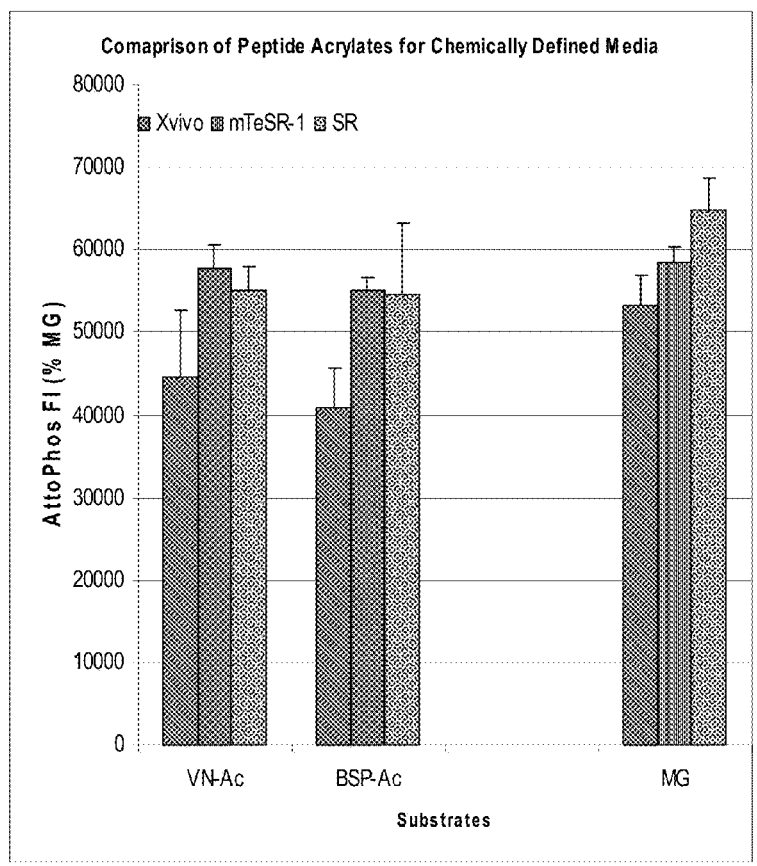
FIG. 9 is a graph illustrating the AttoPhos fluorescence of hESC cells grown on embodiments of the SAP surfaces of the present invention in the presence of different defined media.

Embodiments of SAP surfaces of the present invention were tested for stem cell viability in the presence of several commercially available chemically defined media. FIG. 9 is a graph showing a comparison of AttoPhos fluorescence (expressed as a percentage of Matrigel®) measurements taken from H7 hES cells after 48 hours of culture on XaanProGln-ValThrArgGlyAspValPheThrMetPro (SEQ ID NO:1) (VN) SAP (SAP-VN), XaaGlyGlyAsnGlyGluProArgGl-yAspThrTyrArgAlaTyr (SEQ ID NO:2), (BSP) (SAP-BSP) and control Matrigel® surfaces in the presence of X-Vivo-10 defined media (Geron Corp. Menlo Park, Calif., (Lonza, Cat #04-743Q)) supplemented with 80 ng/ml bFGF (R&D systems, Cat #234-FSE/CF) and 0.5 ng/ml TGFβ1 (R&D systems, Cat. #240B). mTeSR-1 media (Stem Cell Technologies) and SR media (Invitrogen, Carlsbad, Calif.). The SR media is composed of KO-DMEM, 20% KO-SR (Invitrogen, Cat #10828), 1 mM 1-glutamine, 1% NEAA, 0.1 mM 2-ME plus hbFGF at 80 ng/ml and TGFb1 at 0.5 ng/ml. FIG. 9 shows a comparison of H7 cell culture performance using multiple synthetic media.

Cells were cultured for 48 hrs in 96 well plates under standard cell culture conditions (37° C. with 5% $CO_2$) followed by AttoPhos assay (or other assay, as described). For long-term culture on synthetic surfaces, hESC were cultured on described surfaces in 6 wp for at least 10+ consecutive passages in chemically defined media X-Vivo-10 (Geron Corp. Menlo Park, Calif., available from Lonza, Cat #04-743Q)) supplemented with 80 ng/ml bFGF (R&D systems, Cat #234-FSE/CF) and 0.5 ng/ml TGFβ1 (R&D systems, Cat. #240B). Cells were typically passaged every 4-5 days (around 75% confluency) using enzymatic sub-cultivation procedure (collagenase IV treatment), followed by washing with DPBS, scraping and re-suspending in chemically defined culture medium. Cell colony morphology, cell number, viability and hESC-specific marker expression profile relative to cells cultured in parallel with Matrigel surface was assessed at each passage (described below).

7. H7 hESC Cell Proliferation Assays

To evaluate the ability of a polypeptide conjugated to these swellable (meth)acrylates using these conjugation methods to enable hES cell adhesion and proliferation, SAP-VN surfaces were prepared, varying the input peptide concentration from 0-1000 micromolar to create a broad range in peptide densities on the SAP surfaces. These surfaces were compared to SAP-BSP surfaces. Both peptide sequences were conjugated to swellable (meth)acrylate SA02 having 80% hydroxyethyl methacrylate, 20% 2-carboxyethyl acrylate and 3% tetra(ethylene glycol)dimethacrylate (as describe above) and the surfaces were sterilized using EtOH. The experimental plates were sterilized by spraying with 70% ETOH, drying in a laminar hood, and washing five times with 200 µl Dulbecco's Phosphate Buffered Saline (DPBS). H7 hES cells were cultured on these surfaces for 48 hours in Xvivo chemically defined medium (Geron Corp.) supplemented with 80 ng/ml bFGF (R&D systems, Cat #234-FSE/CF) and 0.5 ng/ml TGFβ1 (R&D systems, Cat. #240B). The cells were then fixed and processed for AttoPhos activity using a Promega, assay (Cat. # S1000) to measure alkaline phosphatase activity, which is a known marker for undifferentiated hES cells.

AttoPhos screening was performed as follows. Briefly, at the end of incubation time, cells were rinsed with 150 µl of DPBS and fixed with 4% paraformaldehyde for 10 min at room temperature (70 µl/well of 96-well plate). The cells were washed once with 150 µl of DPBS, and treated for 10 min with 100 µl of AttoPhos fluorescent substrate for alkaline phosphatase (Promega) (diluted 1:3 in DPBS) protected from light. AttoPhos fluorescent intensity at 485/535 nm was obtained using Victor 3 microplate reader (Perklin Elmer). AttoPhos fluorescent intensity for experimental surfaces was expressed as % of MATRIGEL control.

Figure 10:
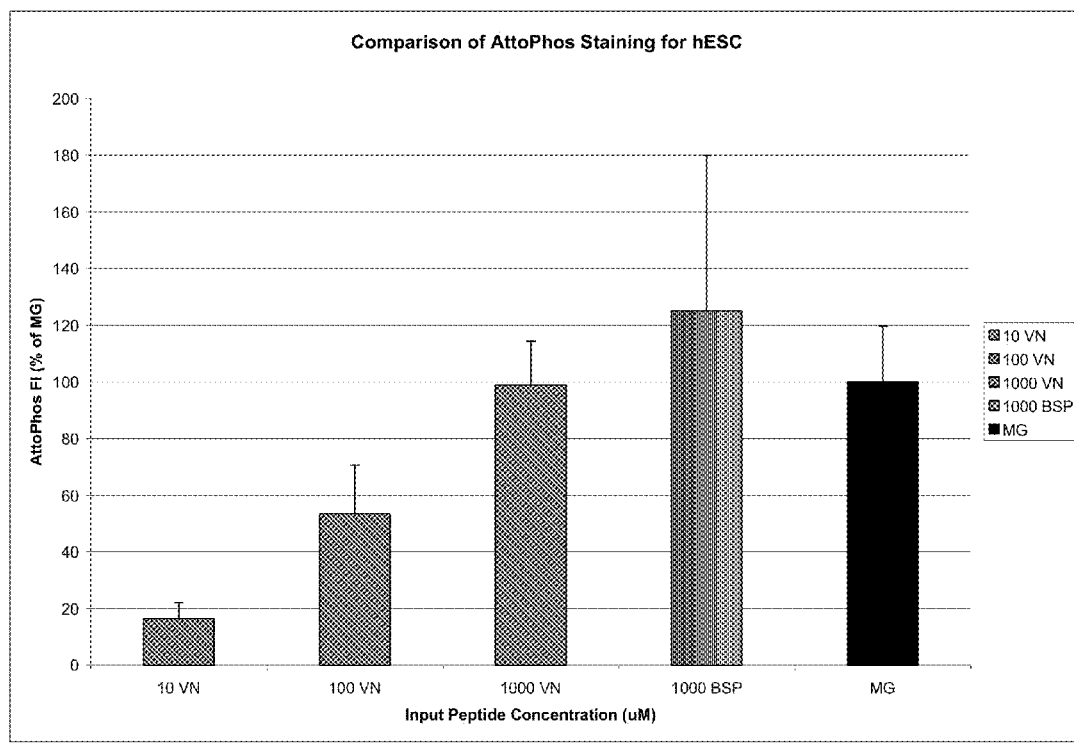
FIG. 10 is a graph showing AttoPhos fluorescence (expressed as a percentage of Matrigel control) for hES cells grown on different embodiments of the SAP surfaces of the present invention.

The AttoPhos fluorescent intensity (FI) for cells on all screened surfaces was normalized to the FI of cells on Matrigel®. As evident in FIG. 10, the surfaces conjugated with input peptide concentration greater than 100 micromolar showed cell attachment comparable to the Matrigel® control.

8. Assays for Cultures of Undifferentiated Stem Cells

Figure 11:
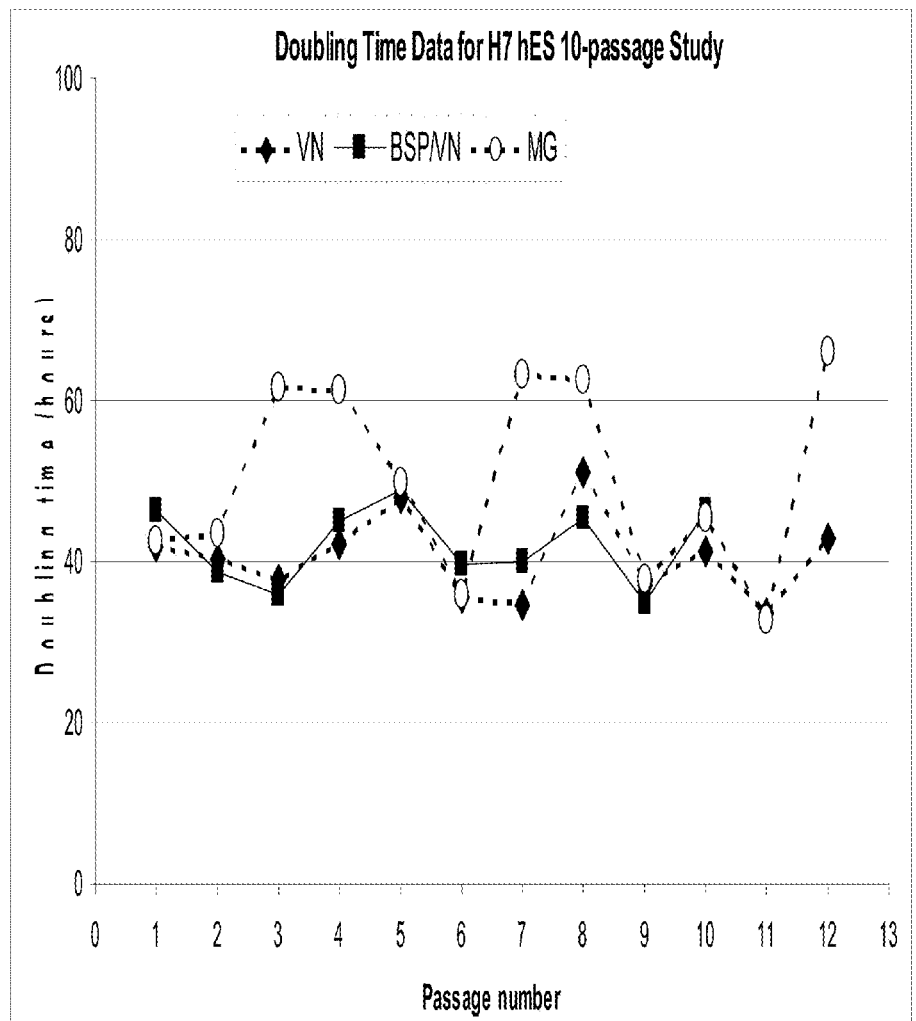
FIG. 11 is a graph showing the doubling time of hES cells growing on embodiments of the SAP surfaces of the present invention

Doubling Time—H7 hES cells were grown on SAP-VN and SAP-VN/BSP (a combination of VN sequence (SEQ ID NO:1 or SEQ ID NO:5) and BSP sequence (SEQ ID NO: 2 or SEQ ID NO:5) coated cell culture substrates and Matrigel® as a control. These cells were allowed to propagate through 10 passages in cell culture. The doubling time (the time required for the population of cells to double) for each passage was measured. FIG. 11 shows the doubling times for embodiments of SAPs of the present invention. These doubling times are comparable to those for cells propagated on Matrigel®.

Figure 12:
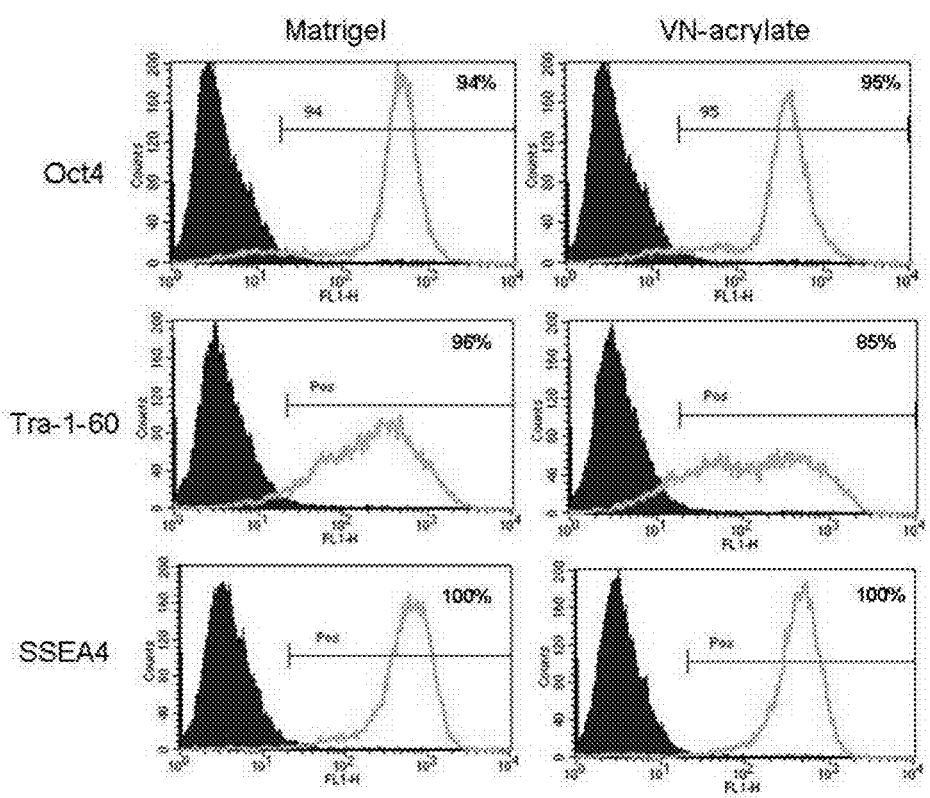
FIG. 12 shows flow cytometry data of gene expression of hES cells growing on embodiments of the SAP surfaces of the present invention

Gene Expression—Expression of known genes Oct4, Tra-1-60 and SSEA4 were measured on the SAP-VN surface, and compared to Matrigel using flow cytometry at the end of each passage. The entire staining procedure was performed at 4° C. Briefly, for each sample $5 \times 10^5$ cells (fixed and permiabilized for Oct4 or live for Tra-1-6- and SSEA4) were re-suspended in 50 microliters of blocking solution (10% HI goat serum in DPBS) and incubated for 15 min, followed by addition of 50 microliter of marker-specific primary antibody (0.5 microgram/sample) or corresponding isotype control (0.5 microgram/sample) in blocking buffer for 30 min. After washing with 2 ml Staining buffer (SB) from BD Biosciences), cells were incubated with corresponding secondary antibody (0.25 microgram/sample) in SB for 30 min protected from light. After washing with SB, cells were stained with PI (2 microgram/ml in SB) for 5 min, for viability assessment. 30,000 gated events (gating was set for PI-negative viable cell population) were acquired for each sample using the FACS Calibur (BD Biosciences). All analyses were done using CellQuest Pro software (BD). FIG. 12 shows that gene expression was similar between H7 hES cells grown on Matrigel and grown on SAP-VN.

Figure 13:
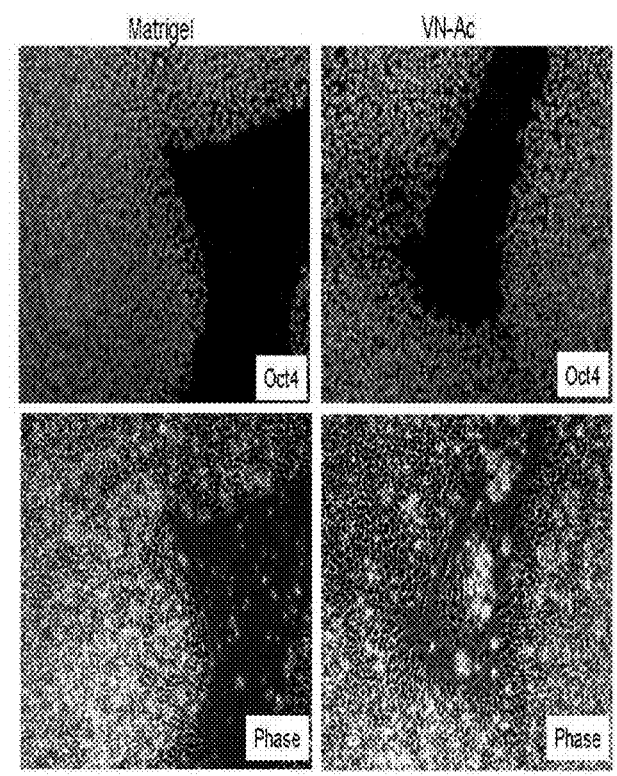
FIG. 13 shows fluorescent images of hES cells growing on embodiments of the SAP surfaces of the present invention compared to Matrigel® control surfaces.

Cell staining—After 4-5 days in culture on synthetic surfaces or Matrigel, cell culture medium was aspirated and cells were washed once with DPBS followed by fixation with 4% PFA for 10 min at R/T. After washing with DPBS, cells were permeablized with 100% EtOH for 2 min (R/T), blocked with 10% heat-inactivated (HI) FBS in DPBS for 1 hr (R/T), followed by three washes with DPBS, and treatment with Oct-4 primary Ab (1 micro gram/ml in 2% HI FBS in DPBS [Chemicon, cat #MAB4401]), or the corresponding isotype control (mouse IgG1) for 1 hr at R/T. Cells were then washed three times with DPBS followed by incubation with corresponding secondary Ab GAM IgG1-AF488 (Invitrogen, cat #A21121) 1:1000 dilution in 2% HI FBS in DPBS plus Hoechst nuclear stain for 30 min at 37° C. protected from light. Finally, cells were washed three times with DPBS and examined with fluorescent microscopy or stored at 4° C. FIG. 13 shows the fluorescence (Oct4) and light microscopic images (Phase) of H7 hES cells grown on Matrigel and on SAP-VN (VN-AC) surfaces. The H7 hES cells grown on SAP-VN surfaces show similar morphology and protein expression to cells grown on Matrigel®.

Figure 14:
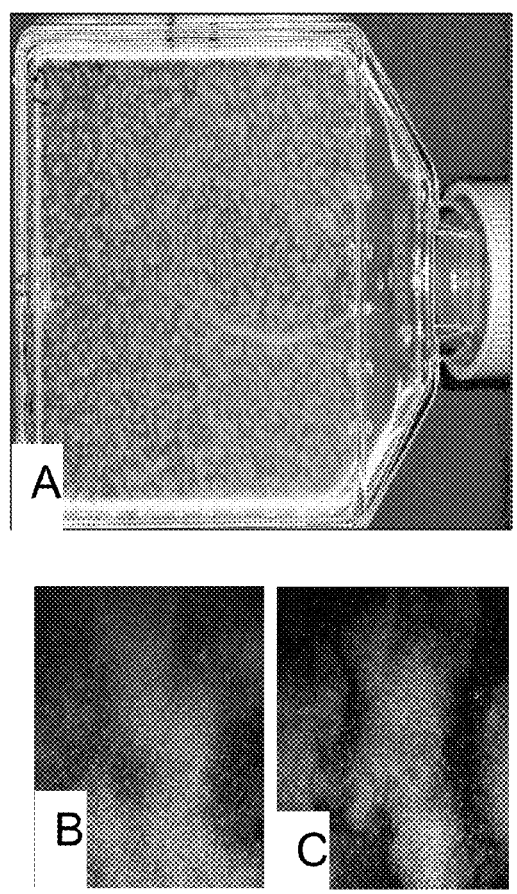
FIG. 14 A-C show images of cells growing on embodiments of the SAP surfaces of the present invention compared to Matrigel® control surfaces.

FIG. 14A shows an optical image of H7 hES cells growing on a T75 flask coated with a SAP-VN coating. FIG. 14B is a micrograph of a representative H7 colony at 2.5× magnification (after 4 days in culture) on a T75 flask coated with 15% SAP-VN. FIG. 14C shows the same magnification of a representative H7 colony grown on a Matrigel® coated flask.

Thus, embodiments of SWELLABLE (METH)ACRYLATE SURFACES FOR CULTURING CELLS IN CHEMICALLY DEFINED MEDIA are disclosed. One skilled in the art will appreciate that the arrays, compositions, kits and methods described herein can be practiced with embodiments other than those disclosed. The disclosed embodiments are presented for purposes of illustration and not limitation.

---

What is claimed is:

1. A method for culturing an isolated population of undifferentiated stem cells comprising:
   providing a synthetic cell culture surface comprising a swellable (meth)acrylate layer, wherein the swellable (meth)acrylate layer is formed from a composition comprising 2-carboxyethylacrylate, tetra(ethylene glycol)dimethacrylate and one of hydroxyethyl methacrylate, hydroxypropyl methacrylate, 2-hydroxyethyl acrylate, 1-vinyl-2-pyrrolidone, di(ethylene glycol) ethyl ether methacrylate, acrylamide, ethylene glycol methyl ether methacrylate or 3-sulfopropyldimethyl-3-methacrylamidopropyl-ammonium; and a peptide comprising an amino acid sequence of XaanProGlnValThrArgGlyAspValPheThrMetPro (SEQ ID NO:1), wherein Xaa is any amino acid and n is an integer from 0 to 3;
   wherein the peptide is conjugated to the swellable (meth)acrylate layer; and,
   wherein the cell culture article has been sterilized by irradiation;
   providing undifferentiated stem cells on the synthetic culture surface;
   culturing the undifferentiated stem cell in chemically defined media; and,
   maintaining undifferentiated stem cells in culture in the chemically defined media for at least five passages.

2. The method of claim 1 wherein the stem cells comprise undifferentiated human embryonic stem cells.

3. The method of claim 2 wherein the stem cells comprise H1 or H7 cells.

4. The method of claim 1, wherein the swellable (meth)acrylate layer is free of polypeptide crosslinkers.

5. The method of claim 1, wherein the swellable (meth)acrylate layer is formed from a composition comprising hydroxyethyl methacrylate, 2-carboxyethyacrylate, and tetra(ethylene glycol)dimethacrylate.

6. The method of claim 1, wherein the swellable (meth)acrylate layer is formed from a composition comprising about 60-90% hydroxyethyl methacrylate by volume, about 10-40% 2-carboxyethyacrylate by volume, and about 1-5% tetra(ethylene glycol)dimethacrylate by volume.

7. The method of claim 5, wherein the volume ratio of hydroxyethyl methacrylate/2-carboxyethylacrylate/tetra(ethylene glycol)dimethacrylate is about 80/20/3.

8. The method of claim 5 wherein the percentage of hydroxyethyl methacrylate/2-carboxyethylacrylate/tetra(ethylene glycol)dimethacrylate in solvent is from 0.1% to 99.5%.

9. The method of claim 5, wherein the swellable (meth)acrylate layer is formed from a composition consisting essentially of hydroxyethyl methacrylate/2-carboxyethylacrylate/tetra(ethylene glycol)dimethacrylate at a volume ratio of about 80/20/3.

10. The method of claim 1, wherein the swellable (meth)acrylate layer is a uniform layer.

11. The method of claim 1, wherein the peptide is conjugated to the swellable (meth)acrylate at a density of greater than about 5 picomoles per square millimeter of a surface of the swellable (meth)acrylate.

12. The method of claim 1 further comprising a peptide comprising an amino acid sequence of LysGlyGlyProGlnValThrArgGlyAspValPheThrMetPro (SEQ ID NO:6).

13. The method of claim 1 wherein the chemically defined medium comprises basic fibroblast growth factor and transforming growth factor-β1.

14. The method of claim 1, wherein the chemically defined medium comprises about 80 ng/ml basic fibroblast growth factor and about 0.5 ng/ml transforming growth factor-β1.

15. The method of claim 1, wherein at least one undifferentiated human embryonic stem cell is maintained in culture in the chemically defined media for at least ten passages.

16. The method of claim 1 the sterilization method is gamma irradiation.

17. The method of claim 16 wherein the gamma irradiation comprises 10-25 kGy treatment.

* * * * *